United States Patent
Etzkorn et al.

(10) Patent No.: US 9,636,050 B1
(45) Date of Patent: May 2, 2017

(54) METHODS AND APPARATUS FOR FORMING A CHANNEL THROUGH A POLYMER LAYER USING A PROTRUSION

(71) Applicant: Verily Life Sciences LLC, Mountain View, CA (US)

(72) Inventors: James Etzkorn, Mountain View, CA (US); Daniel Patrick Barrows, Sunnyvale, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 488 days.

(21) Appl. No.: 14/074,562

(22) Filed: Nov. 7, 2013

(51) Int. Cl.
  *B29D 11/00* (2006.01)
  *A61B 5/145* (2006.01)
  *B32B 3/30* (2006.01)

(52) U.S. Cl.
  CPC ...... *A61B 5/14507* (2013.01); *B29D 11/0073* (2013.01); *B32B 3/30* (2013.01)

(58) Field of Classification Search
  CPC .... B29D 11/0073; A61B 5/14507; B32B 3/30
  See application file for complete search history.

(56) References Cited

U.S. PATENT DOCUMENTS

| | | | |
|---|---|---|---|
| 4,068,933 A | 1/1978 | Seiderman | |
| 4,401,371 A | 8/1983 | Neefe | |
| 4,571,039 A | 2/1986 | Poler | |
| 4,909,818 A | 3/1990 | Jones | |
| 5,044,742 A | 9/1991 | Cohen | |
| 5,626,865 A | 5/1997 | Harris et al. | |
| 6,036,314 A | 3/2000 | Wolfson | |
| 7,591,556 B2 | 9/2009 | Rosenthal | |
| 7,878,650 B2 | 2/2011 | Fritsch et al. | |
| 8,385,998 B2 | 2/2013 | Zhang et al. | |
| 8,506,740 B2 | 8/2013 | Say | |
| 2002/0075447 A1 | 6/2002 | Andino et al. | |
| 2004/0100704 A1 | 5/2004 | Shadduck | |
| 2004/0181172 A1 | 9/2004 | Carney et al. | |
| 2004/0209973 A1 | 10/2004 | Steffen et al. | |
| 2006/0186564 A1 | 8/2006 | Adams et al. | |
| 2006/0265058 A1 | 11/2006 | Silvestrini et al. | |

(Continued)

FOREIGN PATENT DOCUMENTS

| | | |
|---|---|---|
| CN | 201017117 | 2/2008 |
| KR | 1020120010551 | 2/2012 |
| WO | 2004064629 A1 | 8/2004 |

*Primary Examiner* — Mathieu Vargot
(74) *Attorney, Agent, or Firm* — McDonnell Boehnen Hulbert & Berghoff LLP

(57) ABSTRACT

A body-mountable device may include a first polymer layer, a second polymer layer, and a structure that includes a sensor between the first and second polymer layers. Forming the body-mountable device may involve positioning the structure on the first polymer layer and then forming, in a molding piece, the second polymer layer over the structure positioned on the first polymer layer. The molding piece includes a surface that supports the second polymer layer as the second polymer layer is being formed and a protrusion that extends from the surface to the sensor through the second polymer layer as the second polymer layer is being formed. The body-mountable device that is removed from the molding piece has a channel to the sensor formed by the protrusion.

14 Claims, 18 Drawing Sheets

(56) References Cited

U.S. PATENT DOCUMENTS

| | | |
|---|---|---|
| 2006/0290882 A1 | 12/2006 | Meyers et al. |
| 2007/0153231 A1 | 7/2007 | Iuliano |
| 2010/0103369 A1 | 4/2010 | Pugh et al. |
| 2011/0155587 A1 | 6/2011 | Shacham-Diamand et al. |
| 2012/0236524 A1 | 9/2012 | Pugh et al. |
| 2012/0245444 A1 | 9/2012 | Otis et al. |
| 2013/0135578 A1 | 5/2013 | Pugh et al. |
| 2013/0243655 A1 | 9/2013 | Li et al. |
| 2013/0308092 A1 | 11/2013 | Grosiman |
| 2014/0200424 A1 | 7/2014 | Etzkorn et al. |
| 2016/0066825 A1 * | 3/2016 | Barrows .............. A61B 5/1477 600/345 |

* cited by examiner

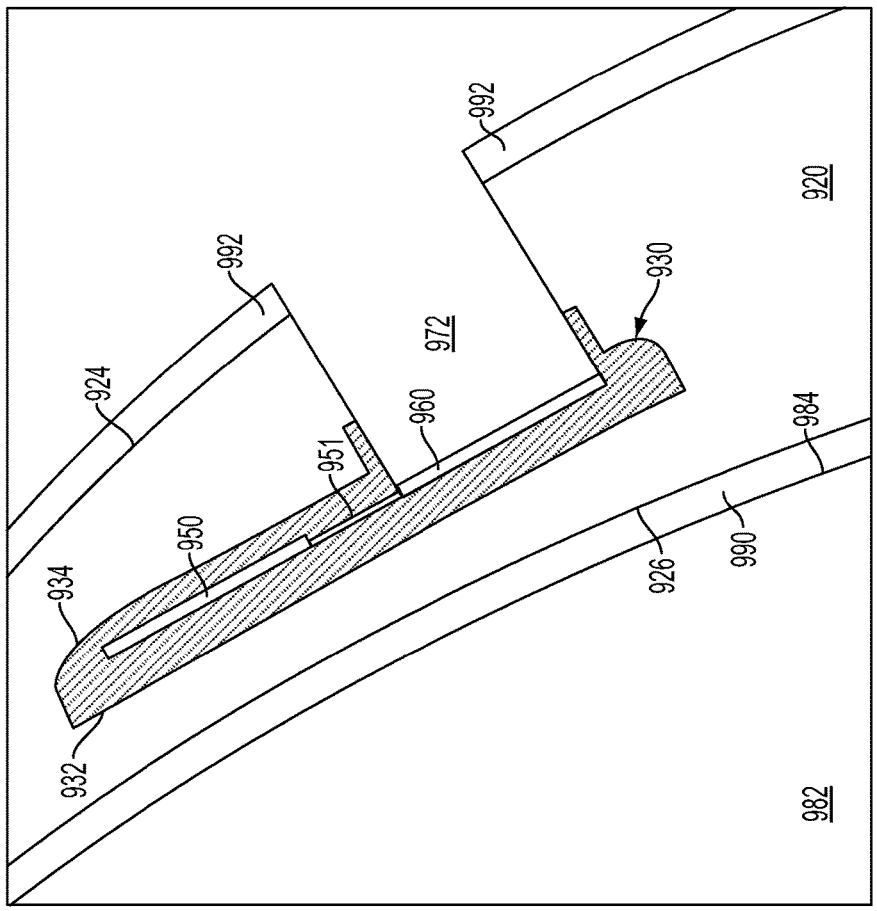
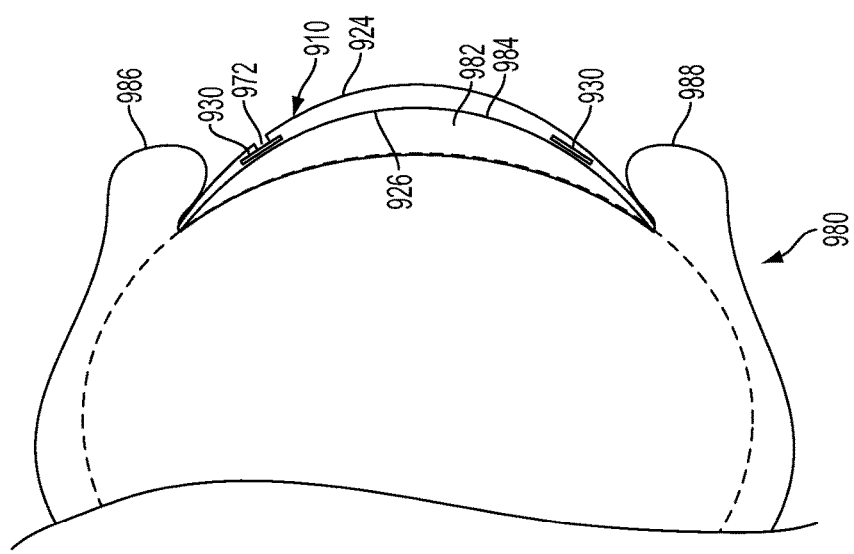
FIG. 9d
FIG. 9c

METHODS AND APPARATUS FOR FORMING A CHANNEL THROUGH A POLYMER LAYER USING A PROTRUSION

BACKGROUND

Unless otherwise indicated herein, the materials described in this section are not prior art to the claims in this application and are not admitted to be prior art by inclusion in this section.

A body-mountable device may be configured to monitor health-related information based on at least one analyte detected in a fluid of a user wearing the body-mountable device. For example, the body-mountable device may comprise an eye-mountable device that may be in the form of a contact lens that includes a sensor configured to detect the at least one analyte (e.g., glucose) in a tear film of a user wearing the eye-mountable device. The body-mountable device may also be configured to monitor various other types of health-related information.

SUMMARY

In one aspect, the present disclosure provides a method. The method involves: forming a first polymer layer; positioning a structure on the first polymer layer, in which the structure includes a sensor; forming, in a molding piece, a body-mountable device by forming a second polymer layer over the structure positioned on the first polymer layer, where the first polymer layer defines a first side of the body-mountable device and the second polymer layer defines a second side of the body-mountable device opposite the first side, and where the molding piece includes a surface that supports the second polymer layer as the second polymer layer is being formed and a protrusion that extends from the surface to the sensor through the second polymer layer as the second polymer layer is being formed; and removing the body-mountable device from the molding piece, where the body-mountable device removed from the molding piece has a channel to the sensor formed by the protrusion.

In another aspect, the present disclosure provides an apparatus for forming a body-mountable device. The body-mountable device includes a first polymer layer defining a first side of the body-mountable device, a second polymer layer defining a second side of the body-mountable device, and a structure that includes a sensor between the first and second polymer layers. The apparatus includes: a first molding piece, where the first molding piece comprises (i) a surface configured to support the second polymer layer as the second polymer layer is being formed and (ii) a protrusion that extends from the surface; and a second molding piece, where the second molding piece is configured to hold the first polymer layer and the structure against the second polymer layer as the second polymer layer is being formed, such that the protrusion contacts the sensor as the second polymer layer is being formed.

In another aspect, the present disclosure provides a body-mountable device. The body-mountable device includes a first polymer layer defining a first side of the body-mountable device; a second polymer layer defining a second side of the body-mountable device; a structure that includes a sensor between the first and second polymer layers; and a molded channel to the sensor.

In yet another aspect, the present disclosure provides a system. The system includes: means for forming a first polymer layer; means for positioning a structure on the first polymer layer, where the structure includes a sensor; means for forming, in a molding piece, a body-mountable device by forming a second polymer layer over the structure positioned on the first polymer layer, where the first polymer layer defines a first side of the body-mountable device and the second polymer layer defines a second side of the body-mountable device opposite the first side, and where the molding piece includes a surface that supports the second polymer layer as the second polymer layer is being formed and a protrusion that extends from the surface to the sensor through the second polymer layer as the second polymer layer is being formed; and means for removing the body-mountable device from the molding piece, where the body-mountable device removed from the molding piece has a channel to the sensor formed by the protrusion.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 9c is a side cross-section view of the eye-mountable device of FIGS. 9a and 9b while mounted to a corneal surface of an eye, according to an example embodiment.

FIG. 9d is a side cross-section view showing the tear film layers surrounding the surfaces of the eye-mountable device mounted as shown in FIG. 9c, according to an example embodiment.

DETAILED DESCRIPTION

The following detailed description describes various features and functions of the disclosed methods, apparatus, and systems with reference to the accompanying figures. In the figures, similar symbols typically identify similar components, unless context dictates otherwise. The illustrative method, apparatus, and system embodiments described herein are not meant to be limiting. It will be readily understood that certain aspects of the disclosed methods, apparatus, and systems can be arranged and combined in a wide variety of different configurations, all of which are contemplated herein.

I. Introduction

A body-mountable device may be configured to monitor health-related information based on at least one analyte detected in a fluid of a user wearing the body-mountable device. Such a body-mountable device may include a sensor configured to detect the at least one analyte. The sensor can receive the at least one analyte through a channel to the sensor in a polymer layer of the body-mountable device. Such a body-mountable device may be formed (e.g., fabricated) in a molding piece that includes a surface that supports the polymer layer as the polymer layer is being formed and a protrusion that extends from the surface to the sensor through the polymer layer as the polymer layer is being formed. With this arrangement, the channel may be formed by the protrusion.

Beneficially, embodiments described herein may help to improve the manufacturability of the channel. For instance, formation of body-mountable devices in accordance with an example embodiment may allow for repeatable dimension(s) of the channel and/or placement of the channel through the polymer layer for a plurality of body-mountable devices. And formation of body-mountable devices in accordance with an example embodiment may allow for the channel to have uniform dimensions. In addition, embodiments described herein could help to improve the comfort of a wearer of the body-mountable device.

As used throughout this disclosure, the anterior side of the body-mountable device refers to an outward-facing side of the body-mountable device, whereas the posterior side of the body-mountable device refers to an inward-facing side of the body-mountable device. In particular, when the body-mountable device comprises an eye-mountable device and the eye-mountable device is mounted on an eye of the user, the anterior side corresponds to a side of the eye-mountable device that is facing outward and thus not touching the eye of the user. Further, when the eye-mountable device is mounted on an eye of the user, the posterior side corresponds to a side of the eye-mountable device that is facing inward and thus touching the eye of the user.

II. Example Methods

Figure 1:
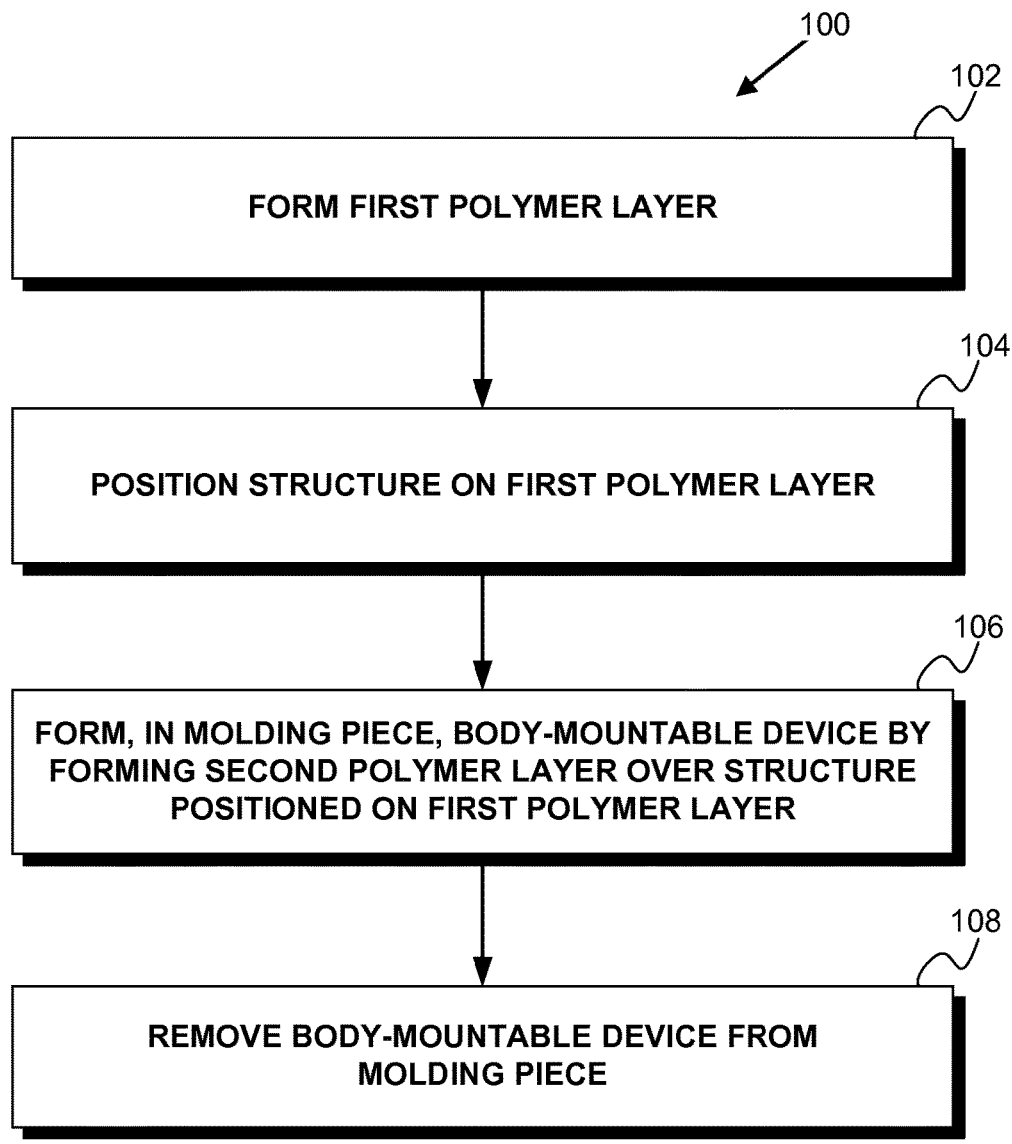
FIG. 1 is a flow chart illustrating a method according to an example embodiment.

Example methods for forming a body-mountable device are disclosed. FIG. 1 is a flow chart illustrating a method 100 according to an example embodiment. More specifically, as shown by block 102, the method 100 may involve forming a first polymer layer. Further, as shown by block 104, the method 100 may involve positioning a structure on the first polymer layer, wherein the structure comprises a sensor. Further still, as shown by block 106, the method 100 may involve forming, in a molding piece, a body-mountable device by forming a second polymer layer over the structure positioned on the first polymer layer, wherein the first polymer layer defines a first side of the body-mountable device and the second polymer layer defines a second side of the body-mountable device opposite the first side, and wherein the molding piece comprises a surface that supports the second polymer layer as the second polymer layer is being formed and a protrusion that extends from the surface to the sensor through the second polymer layer as the second polymer layer is being formed. And, as shown by block 108, the method 100 may involve removing the body-mountable device from the molding piece, wherein the body-mountable device removed from the molding piece has a channel to the sensor formed by the protrusion.

Figure 2:
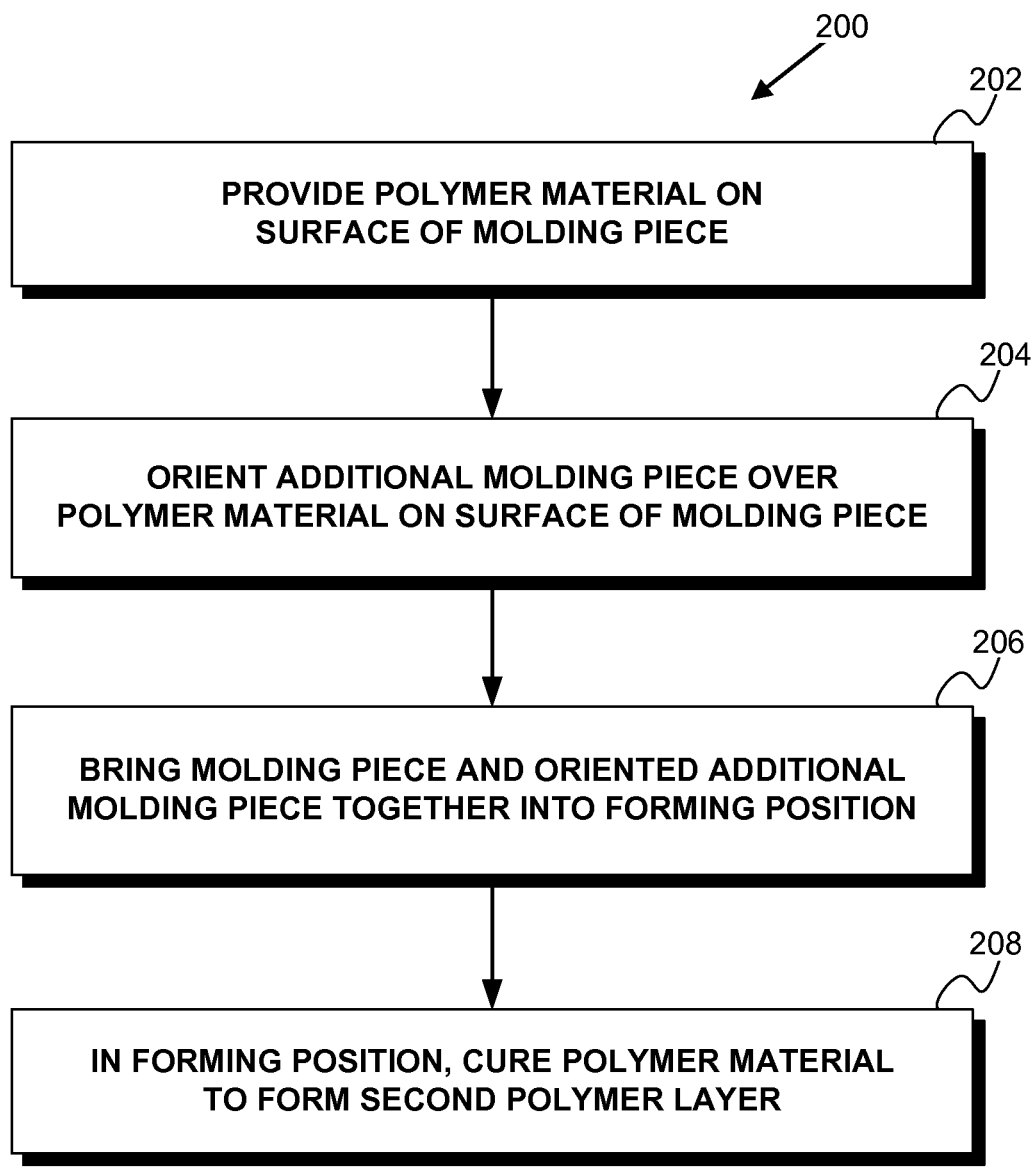
FIG. 2 is a flow chart illustrating another method according to an example embodiment.

In addition, FIG. 2 is a flow chart illustrating another method 200 according to an example embodiment. The method 200 may be performed in connection with block 106 of method 100. More specifically, as shown by block 202, the method 200 may involve providing a polymer material on the surface of the molding piece. Further, as shown by block 204, the method 200 may involve orienting an additional molding piece over the polymer material on the surface of the molding piece, wherein the additional molding piece holds the structure positioned on the first polymer layer, and wherein the orienting of the additional molding piece positions the sensor directly above the protrusion. Further still, as shown by block 206, the method 200 may involve bringing the molding piece and the oriented additional molding piece together into a forming position, wherein in the forming position (i) the polymer material on the surface of the molding piece contacts the structure and the first polymer layer held by the additional molding piece and (ii) the sensor contacts the protrusion. And, as shown by block 208, the method 200 may involve in the forming position, curing the polymer material to form the second polymer layer.

For purposes of illustration, the method 100 and the method 200 are described below as being carried out by a fabrication device that utilizes cast or compression molding, among other processes. It should be understood, however, that the method 100 and/or the method 200 may be carried out by a fabrication device that utilizes other methods and/or processes for forming body-mountable devices.

Moreover, for purposes of illustration, the method 100 and the method 200 are described below in a scenario where a body-mountable device comprises an eye-mountable device. It should be understood, however, that the method 100 and/or the method 200 may involve scenarios where the body-mountable device comprises other mountable devices that are mounted on or in other portions of the human body. For example, the body-mountable device may comprise a tooth-mountable device and/or a skin-mountable device.

A. Forming a First Polymer Layer

Figure 3A:
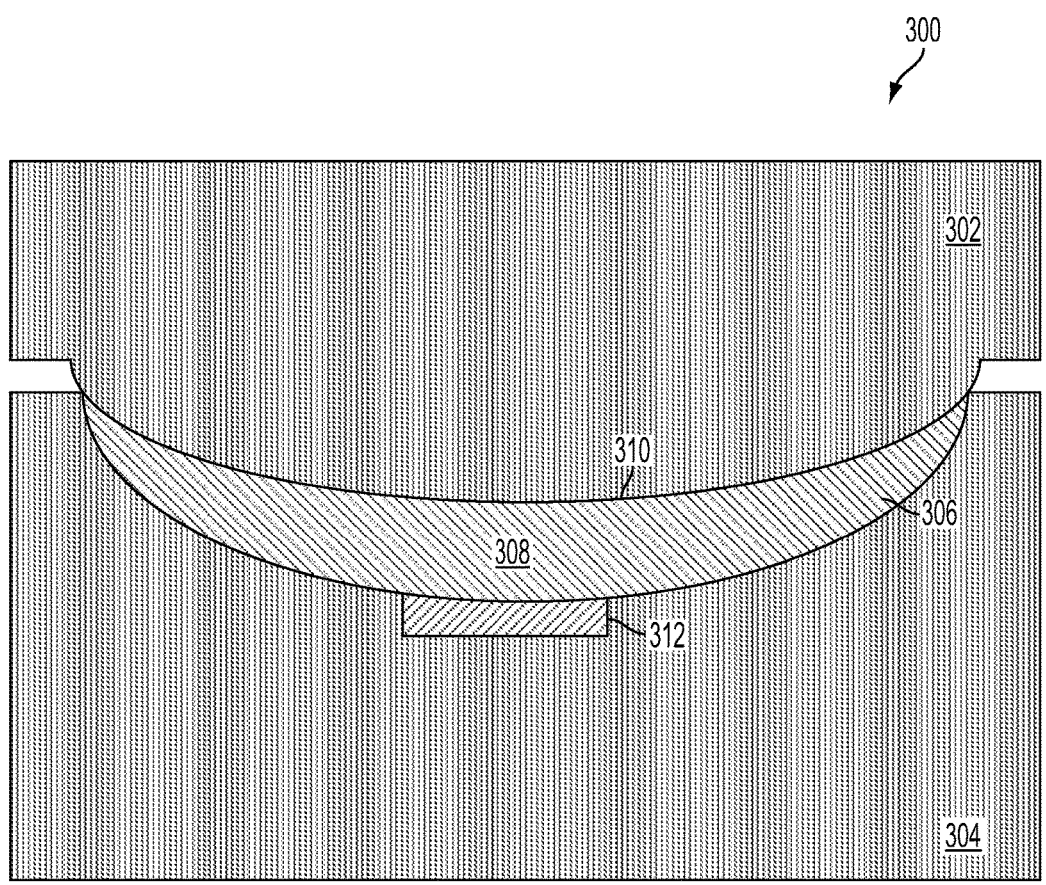
FIG. 3a is an illustration of formation of a first polymer layer, according to an example embodiment.

As mentioned above, at block 102, the fabrication device may be used to form a first polymer layer. The fabrication device may include molding pieces, such as molding pieces that are suitable for cast molding. FIG. 3a illustrates a fabrication device 300 that includes molding pieces that may be used to form the first polymer layer. In particular, FIG. 3a illustrates the fabrication device 300 including a first molding piece 302 and a second molding piece 304. The first molding piece 302 and the second molding piece 304 may define a first cavity. A polymer material 306 may be provided on a surface of the second molding piece 304, and the polymer material 306 may be compressed into a first polymer layer 308 by the first molding piece 302. In an example, the polymer material 306 may be provided on the surface of the second molding piece 304 by filling the second molding piece 304 with the polymer material 306.

After the polymer material 306 is compressed into the first polymer layer 308, the fabrication device 300 may cure the first polymer layer 308. In an example, the polymer material 306 can be a light-curable polymer material, and the fabrication device 300 may be configured to cure the light-curable polymer material using light, such as ultraviolet light or visible light. In an example, the first polymer layer 308 may be cured to a partially-cured state. In such an example, this may involve curing the material to a partially-cured state that is approximately 50-75% of a fully cured state. Other partially-cured states are possible as well. Beneficially, by partially curing the first polymer layer 308 to a partially-cured state, the first polymer layer 308 may have a tackiness that facilitates adhesion thereto. With this arrangement, the tackiness may ensure that a structure placed on the first polymer layer 308 remains securely fixed in a given location during subsequent formation steps.

The tackiness exhibited by the partially-cured first polymer layer 308 may be different for different polymers. Accordingly, the fabrication device 300 may be configured to cure different polymer materials differently than other polymer materials (e.g., a first polymer material may be cured more than a second polymer material). Further, in addition to light curing, other methods of curing are possible as well, such as chemical additives and/or heat. For instance, the first polymer material may be cured at a certain temperature, such as between 100 degrees Celsius (C.) to 150 degrees C. Yet still further, in other example embodiments, the first polymer layer 308 may be completely cured. Alternatively, the fabrication device 300 may bypass curing the first polymer layer 308 at this stage.

The first molding piece 302 and the second molding piece 304 may be configured to achieve a given desired thickness of the first polymer layer 308. For instance, in an example, the first polymer layer 308 can have a thickness of less than 150 micrometers. In an example embodiment, the first molding piece 302 and the second molding piece 304 can be designed so as to allow for a layer having less than a 150 micrometer thickness between the two cavities. As such, when the first molding piece 302 and the second molding piece 304 are pressed together during the formation of the first polymer layer 308, the resulting polymer layer 308 will have a thickness of less than 150 micrometers.

In an example, the thickness of the first polymer layer 308 can be selected based on a particular analyte or analytes an eye-mountable device is configured to detect. For example, an optimal thickness for a first analyte may be 10 micrometers, while an optimal thickness for a second analyte may be 25 micrometers. Other examples are possible as well.

In an example, the polymer material 306 can be any material that can form an eye-compatible polymer layer. For example, the polymer material 306 may be a formulation containing polymerizable monomers, such as hydrogels, silicone hydrogels, silicone elastomers, and rigid gas permeable materials. Further, the polymer material 306 may form a transparent or substantially transparent polymer layer. As such, the use of the polymer material 306 may result in an eye-mountable device through which the wearer can see when mounted on the wearer's eye. In an example, the polymer material 306 can be a hydrogel material, such as silicone hydrogel. As known in the art, hydrogel materials are commonly used in contact-lens technology and are well-suited for eye-mountable devices. Other materials are possible as well.

In an example, the first molding piece 302 and/or the second molding piece 304 can be configured so as to allow sufficient pinch off to provide for suitable edges for an eye-mountable device.

Further, in an example, the first molding piece 302 and the second molding piece 304 may be transparent, such that the polymer material 306 may be visible during formation of the first polymer layer 308. Such an arrangement may assist in orienting the first molding piece 302 and/or the second molding piece 304.

The first polymer layer 308 defines a posterior side (or a first side) 310 of an eye-mountable device. That is, the first polymer layer 308 defines an outer edge of the eye-mountable device. When mounted on an eye of a user, the posterior side 310 of the eye-mountable device defined by the first polymer layer 308 corresponds to a side of the device touching the eye of the user. The first molding piece 302 may be shaped so as to define a shape of the posterior side 310. For example, a curvature of the posterior side 310 may be defined by the first molding piece 302.

The first polymer layer 308 can further comprise an alignment feature 312. In an example, the alignment feature 312 can comprise an asymmetric peg. The asymmetric peg can be a variety of shapes. For instance, the asymmetric peg can have a star-shaped or cross-shaped cross section. Other shapes of the asymmetric peg are possible as well.

As mentioned above, although FIG. 3a illustrates forming the first polymer layer 308 through cast molding, other methods for forming the first polymer layer 308 are possible as well. For example, the first polymer layer 308 may be formed via injection molding. In injection molding, rather than polymer material being compressed between molding pieces, molding material may be heated and injected or otherwise forced into a molding piece or pieces. The injected molding material may then cool and harden to the configuration of the molding piece or pieces.

As another example, the first polymer layer 308 may be formed via spin casting. Through spin-casting techniques, the fabrication device 300 may form a first polymer layer of a precise thickness. In an example, a spin-casting mold may be spun along its central access at a set speed, and the polymer may be introduced to the mold as the mold is spinning in order to form a first polymer layer. The final thickness of the first polymer layer may be influenced by various factors, including but not limited to the spin-casting mold, the amount of polymer introduced to the spin-casting mold, properties of the polymer such as viscosity, and/or the speed at which the spin-casting mold is rotated. These factors may be varied in order to result in a first polymer layer of a well-defined thickness.

B. Positioning a Structure on the First Polymer Layer

Figure 3B:
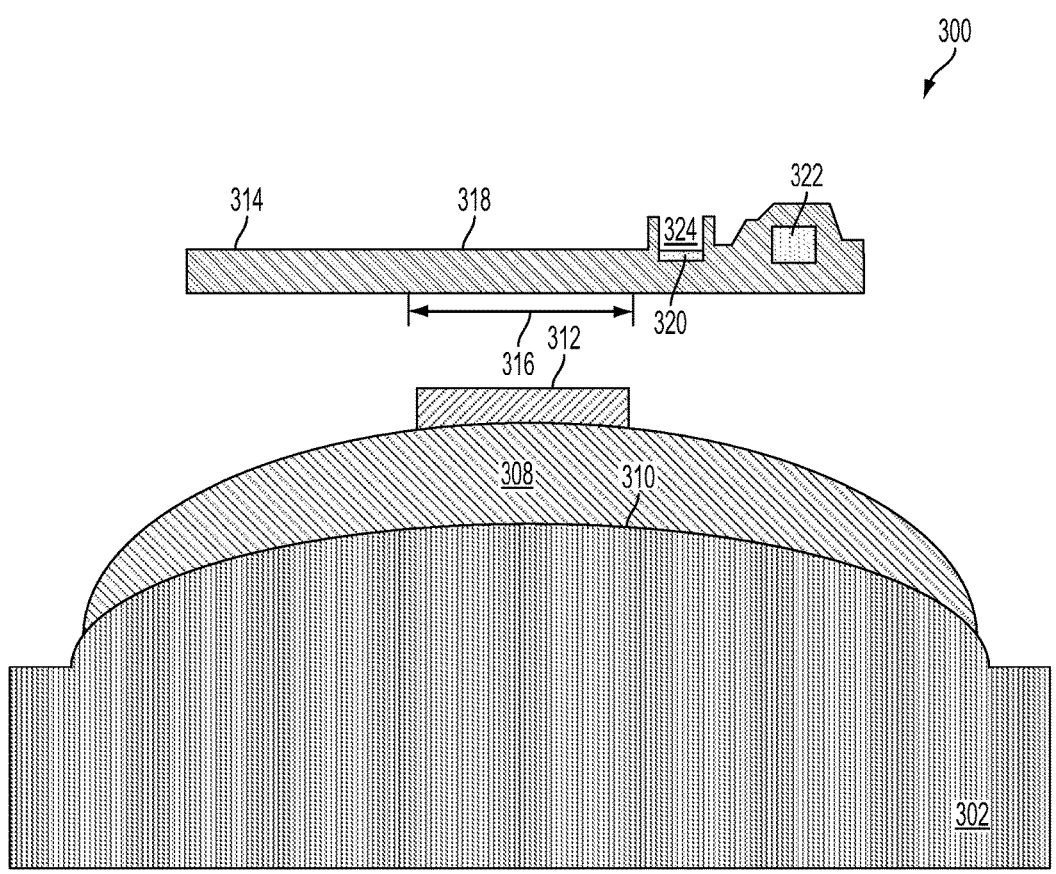
FIG. 3b is an illustration of positioning a structure on a first polymer layer, according to an example embodiment.
Figure 3C:
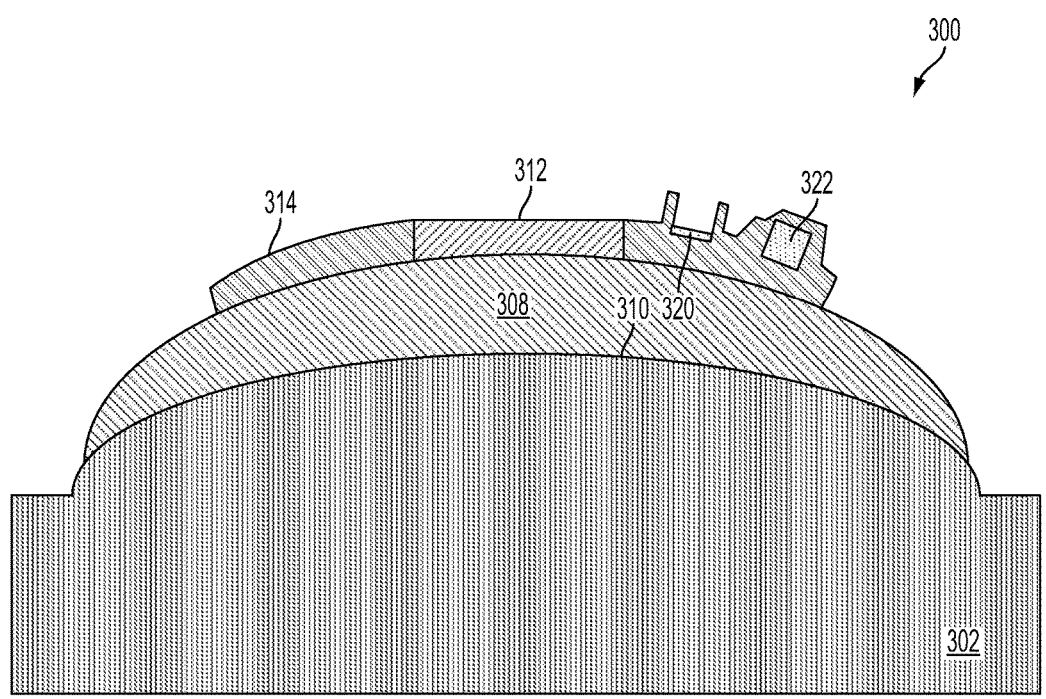
FIG. 3c is an illustration of a structure positioned on a first polymer layer, according to an example embodiment.

As mentioned above, at block 104, a structure may be positioned on the first polymer layer. FIGS. 3b and 3c illustrate an example in which a structure 314 is positioned on the first polymer layer 308.

In an example, the structure 314 has an outer diameter and a hole 316 that defines an inner diameter. And the structure 314 includes a polymer 318, a sensor 320, and electronics 322. The structure 314 may occupy a peripheral portion of an eye-mountable device, such as an eye-mountable device 400 illustrated in FIG. 4, so as to limit interference with a user's field of view when the eye-mountable device is mounted on an eye of the user. The polymer 318 may comprise a variety of polymeric materials, such as paralyene.

In the illustrated example, the electronics 322 is embedded in the polymer 318, and the sensor 320 is surrounded by the polymer 318, except for the sensor 320 being exposed by an opening 324. However, in other examples, the sensor 320 and electronics 322 may be mounted on a surface of the polymer 318, such as a top surface of the polymer 318. With this arrangement, the structure 314 might not include the opening 324. In some embodiments, the opening 324 can have a dimension of between 500 to 700 micrometers. Other dimensions are possible as well. And, in some embodiments, the opening 324 can have a square shape with rounded corners. Other shapes are possible as well, such as rectangular, circular, etc.

The structure 314 can have various sizes. For instance, the size of the structure 314 may depend on which analyte (or analytes) an eye-mountable device is configured to detect. In an example, the structure 314 is a substrate shaped as a ring with an outer diameter of approximately a 1 centimeter, a radial thickness of approximately 1 millimeter, and a maximum height of approximately 50 between 150 micrometers. Of course, other sizes of the structure 314 are possible as well.

In an example, the structure 314 has a height dimension of at least 50 micrometers. In other words, at some point of the structure 314, the height of the structure 314 may be at least 50 micrometers. In such an example, this height dimension may correspond to a maximum height of the structure 314. In accordance with this disclosure, the maximum height of the structure 314 corresponds to the height of the structure 314 at its highest point. For instance, in the example where the structure 314 includes the sensor 320 and the electronics 322, the height of the structure 314 may vary (and thus the structure 314 may have various height dimensions). For example, the height of the structure 314 may be higher at a point where the electronics 320 is mounted on the structure 314, whereas the height may be lower at a point where the electronics 320 is not mounted on the structure 322. In such an example, the maximum height may correspond to the point where the electronics 322 is located on the structure 314. Further, in an example, the structure 314 can be more rigid than the first polymer layer 308.

The sensor 320 can be configured in a variety of ways. As one example, the sensor 320 may comprise a pair of electrodes, such as a working electrode and a reference electrode, configured to detect one or more analytes. Other configurations of the sensor 320 are possible as well. And the sensor 320 can have a variety of thicknesses. As one example, the sensor 320 can have a thickness of 260 nanometers. Other thicknesses of the sensor 320 are possible as well.

The electronics 322 can be configured in a variety of ways. As one example, the electronics 322 can comprise a chip including one or more logic elements configured to operate the sensor 320. Other configurations of the electronics 322 are possible as well.

In order to position the structure 314, the fabrication device 300 may separate the first molding piece 302 from the second molding piece 304. When the fabrication device 300 separates the first molding piece 302 from the second molding piece 304, the first polymer layer 308 may stick to a side of the first molding piece 302. In an example, the first polymer layer 308 and/or the first molding piece 302 can be surface treated, such that the first polymer layer 308 sticks to the side of the first molding piece 302. Additionally or alternatively, the second molding piece 304 can be surface treated, such that the first polymer layer 308 sticks to the side of the first molding piece 302.

In an example, positioning the structure 314 on the first polymer layer 308 can include aligning the structure 314 with the alignment feature 312. In one example, the hole 316 in the structure 314 has an asymmetric inner diameter and the alignment feature 312 includes an asymmetric peg such that the hole 316 receives the alignment feature 312 in only a predetermined rotational orientation. However, other ways of providing a predetermined rotational orientation of the structure 314 by alignment with the alignment feature 312 are also possible.

Alternatively, the fabrication device 300 can include a positioning apparatus (not shown), such as a robotic system, configured to position the structure 314 on the first polymer layer 308 in a predetermined rotational orientation. For instance, the positioning apparatus may (i) pick up the structure 314 (e.g., via suction), (ii) position the structure 314 above the first polymer layer 308, and then (iii) lower the structure 314 toward the first polymer layer 308. When the structure 314 is positioned in a predetermined rotational orientation, the positioning apparatus may then release the structure 314 (e.g., by releasing the suction). With this approach, the first polymer layer 308 might not include the alignment feature 312.

In some embodiments, the positioning apparatus may bend the structure 314. The positioning apparatus may bend the structure 314 by applying a force and/or a torque to one or more portions of the structure 314.

The positioning apparatus may further include a vision system configured to assist with positioning the structure 314 on the first polymer layer 308. Such a vision system may facilitate guiding the structure 314 to a precise location on the first polymer layer 308. In an example, the vision system can be appropriate for situations in which one or more production specifications for an eye-mountable device, such the eye-mountable device 400, have requirements with very low tolerances related to the positioning of a sensor, such as the sensor 320, within the eye-mountable device.

During formation of an eye-mountable device, such as the eye-mountable device 400, it may be desirable for the structure 314 to remain in a fixed position during formation of the eye-mountable device. For instance, movement of the structure 314 during subsequent formation steps, such as formation of a second polymer layer, may result in improper placement of the structure 314 relative to the surrounding polymer layers. As one example, movement of the structure 314 during providing a molding piece with a polymer material to form the second polymer layer and/or curing the second polymer layer can result in improper placement of the structure 314 relative to the surrounding polymer layers.

Therefore, in an example, an adhesive is applied to the structure 314 and/or the first polymer layer 308 before the structure 314 is placed on the first polymer layer 308. The applied adhesive may facilitate adhesion of the structure 314 to the first polymer layer 308. For instance, a small amount of adhesive may be applied to a cured first polymer layer 308, and the structure 314 may be positioned on the small amount of adhesive such that the structure 314 adheres to the first polymer layer 308. Additionally or alternatively, a small amount of adhesive may be applied to the structure 314, and the structure 314 may then be placed on the first polymer layer 308 (e.g., a cured first polymer layer) such that the structure 314 adheres to the first polymer layer 308. With this arrangement, the structure 314 may remain adhered to the first polymer layer 308 in a secure location during subsequent formation steps.

As noted above, in an example, the first polymer layer 308 in a partially-cured state may have a tackiness that facilitates adhesion thereto. With this arrangement, the structure 314 may remain adhered to the first polymer layer 308 in a secure location during subsequent formation steps.

In some situations, such as for large-scale production purposes, it may be desirable to not only place the structure 314 in a predetermined rotational orientation, but it may also be desirable to repeatedly place and maintain the structure 314 at this precise location for a plurality of eye-mountable devices. Beneficially, formation of an eye-mountable device in accordance with an example embodiment allows for such repeatable and precise positioning.

FIG. 3c illustrates the structure 314 positioned on the first polymer layer 308. With this arrangement, the sensor 320 may be mounted at a particular angle along a circumference of the first polymer layer 308. As a result, the sensor 308 may be placed at a precise location in an XYZ plane on the first polymer layer 308. As one example, the sensor 320 may rest at a 6 o'clock position of the first polymer layer 320. As another example, the sensor 320 may rest at a 12 o'clock position of the first polymer layer 308.

Figure 3D:
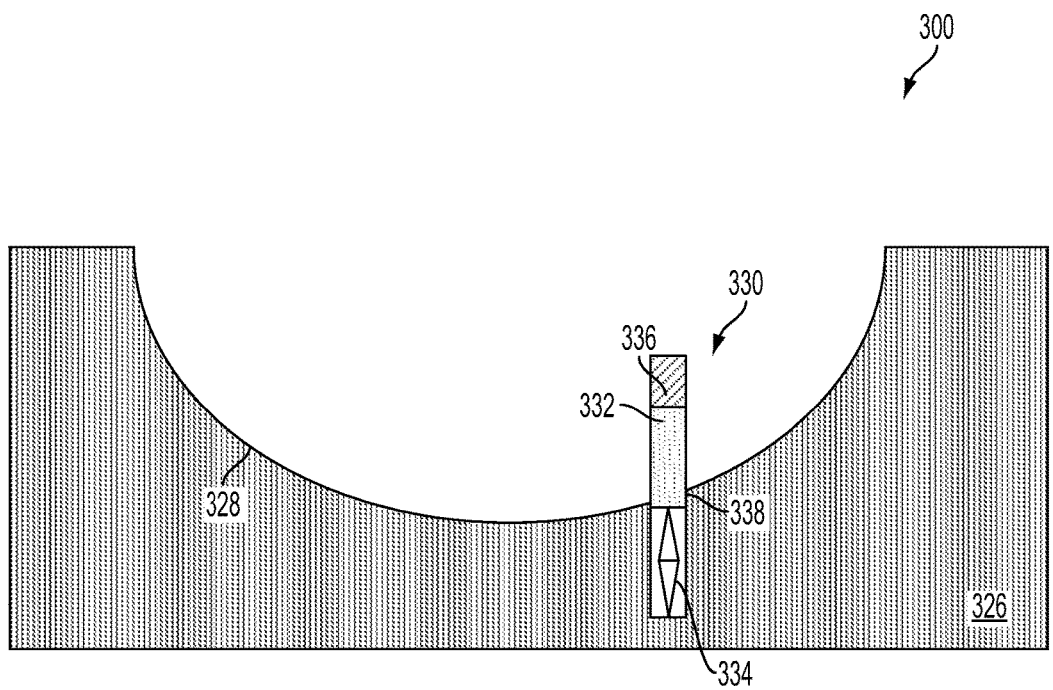
FIG. 3d is an illustration of a molding piece, according to an example embodiment.

C. Forming, in a Molding Piece, a Body-Mountable Device by Forming a Second Polymer Layer Over the Structure Positioned on the First Polymer Layer As mentioned above, at block 106, the fabrication device may form a body-mountable device by forming a second polymer layer over the structure positioned on the first polymer layer. FIGS. 3d-3i illustrate the fabrication device 300 including molding pieces that may be used to form the second polymer layer. In particular, FIG. 3d illustrates a third molding piece 326. The first molding piece 302 and the third molding piece 326 may define a second cavity. In some embodiments, the molding piece of the method 100 and/or the method 200 may take the form of or be similar in form to the third molding piece 326.

Figure 3E:
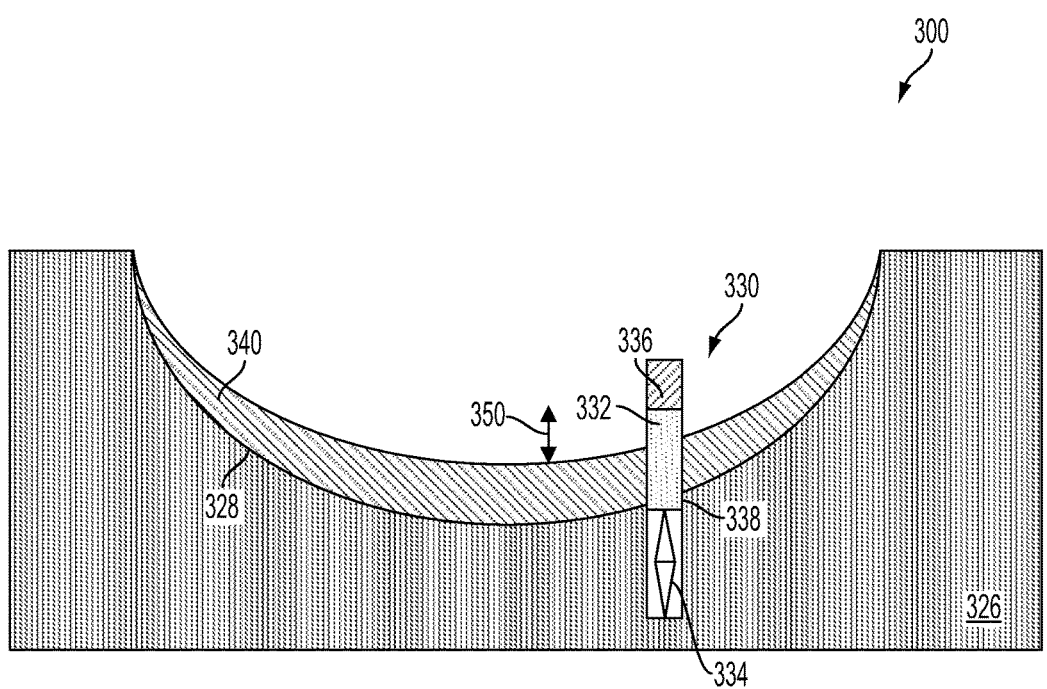
FIG. 3e is an illustration of providing a polymer material on a surface of the molding piece, according to an example embodiment.
Figure 3F:
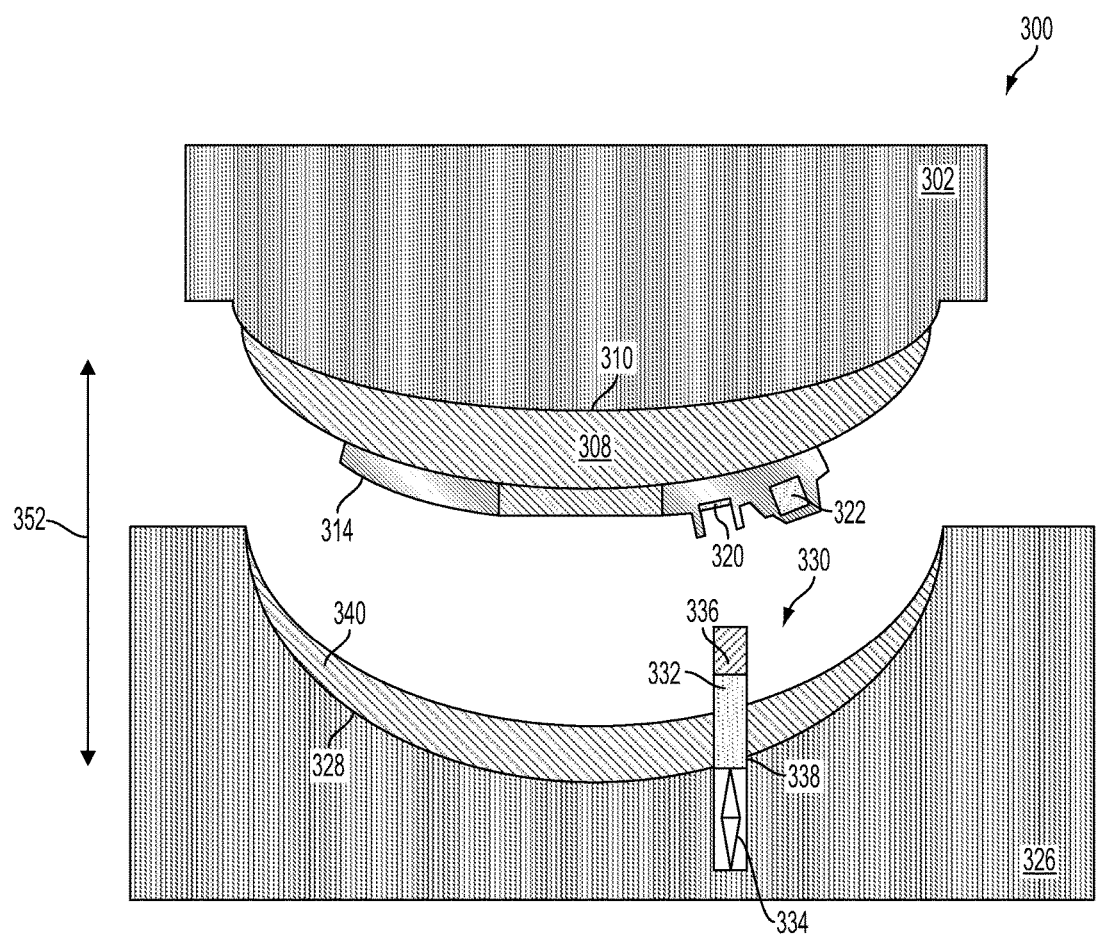
FIG. 3f is an illustration of orienting an additional molding piece over the polymer material on the surface of the molding piece, according to an example embodiment.
Figure 3G:
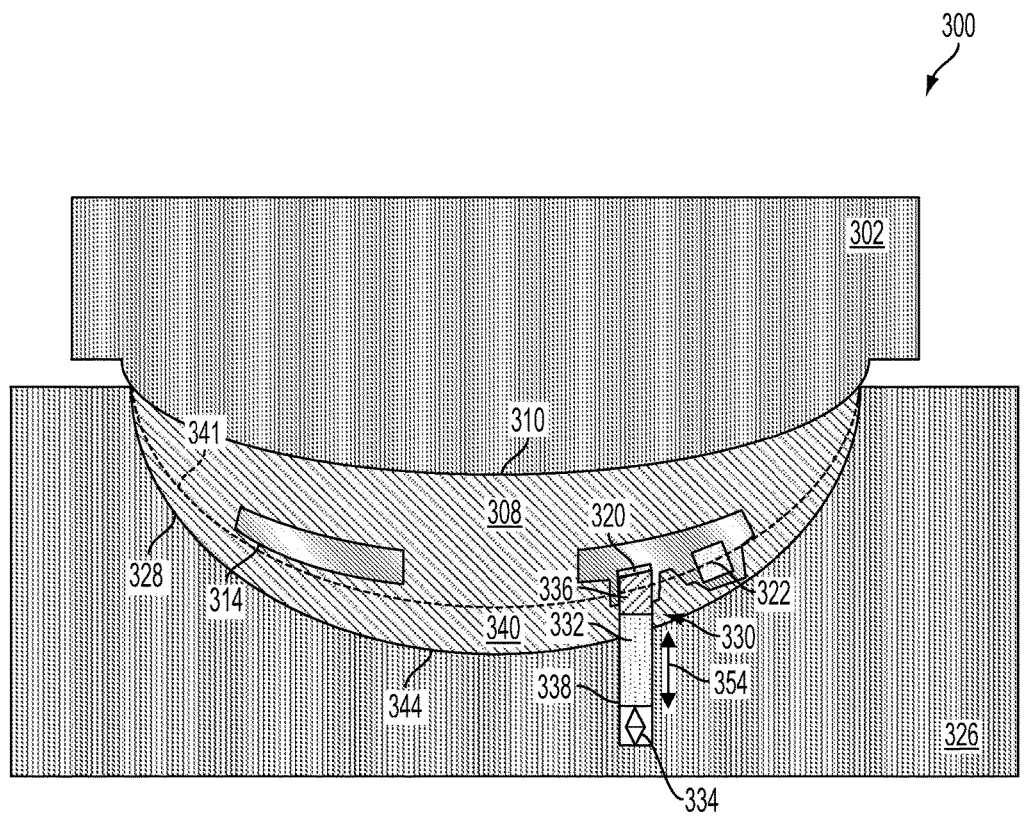
FIG. 3g is an illustration of bringing the molding piece and the oriented additional molding piece together into a forming position, according to an example embodiment.
Figure 3H:
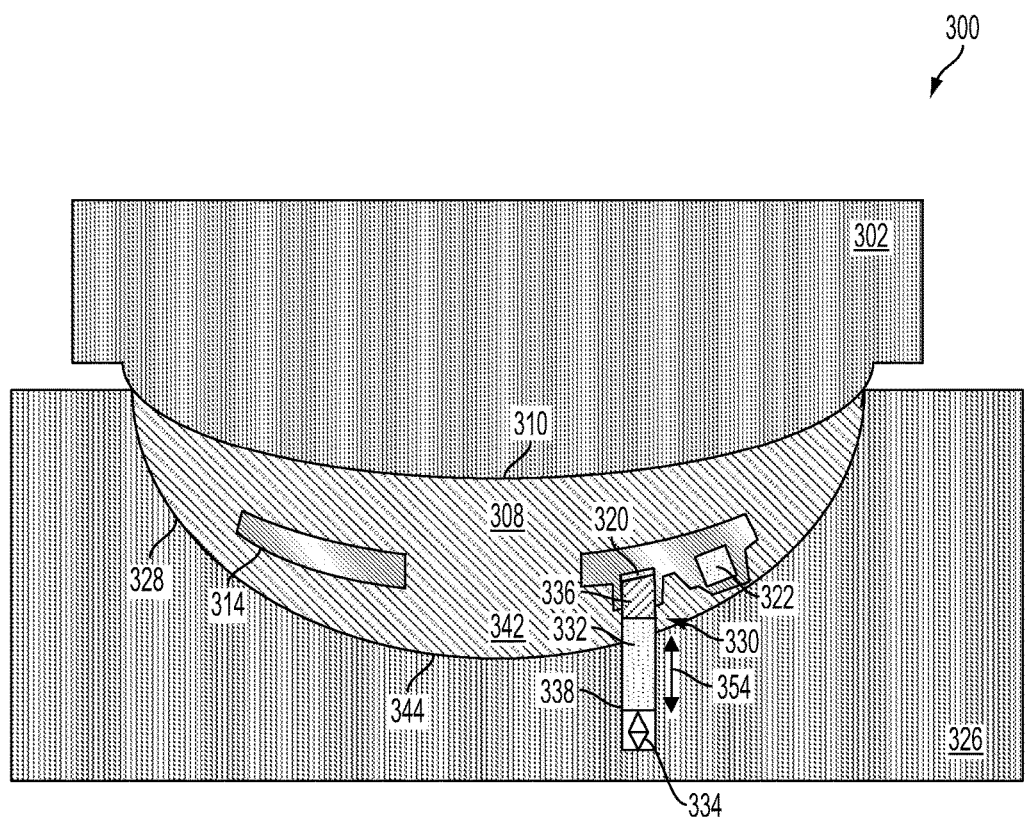
FIG. 3h is an illustration of in the forming position, curing the polymer material to form a second polymer layer, according to an example embodiment.
Figure 3I:
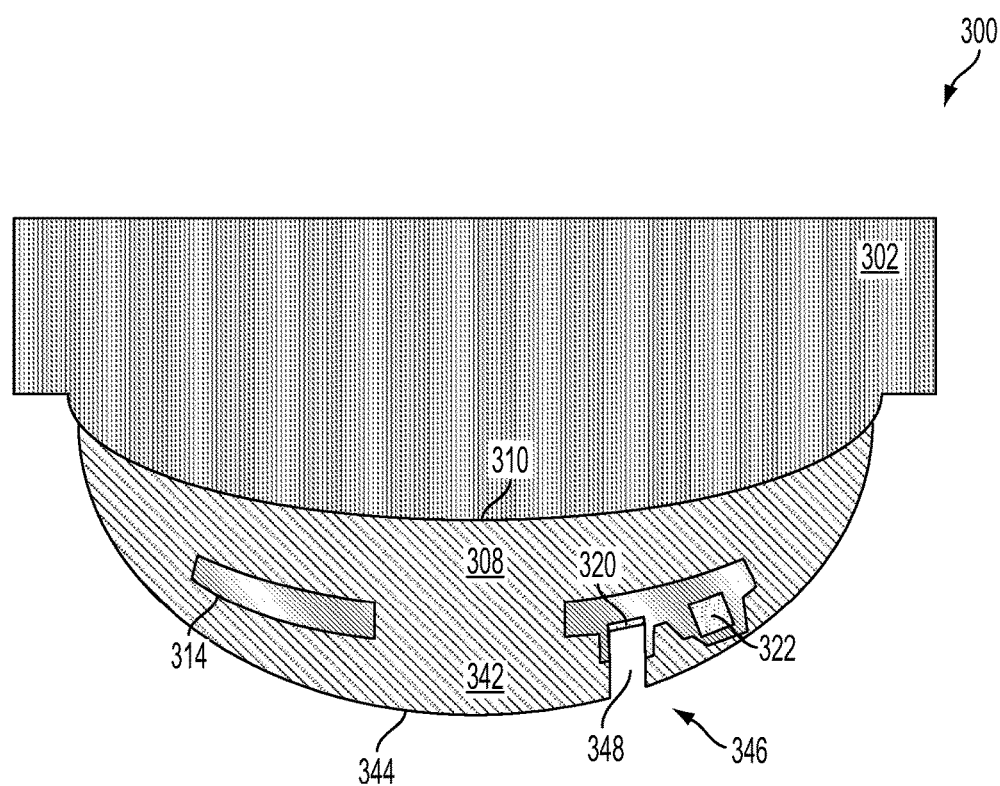
FIG. 3i is an illustration of removing an eye-mountable device from the molding piece, according to an example embodiment.

As shown in FIG. 3d, the third molding piece 326 includes a surface 328 that supports a second polymer layer 342 (as shown in FIGS. 3h and 3i) as the second polymer layer 342 is being formed and a protrusion 330 that extends from the surface 328 to the sensor 320 through the second polymer layer 342 as the second polymer layer 342 is being formed (as shown in FIG. 3h).

Further, as shown in FIG. 3d, the protrusion 330 may include a rod 332 and a spring 334. The rod 332 may have a first end 336 and a second end 338, and the spring 334 may be connected to the second end 338 of the rod 332 and configured to press the first end 336 of the rod 332 against the sensor 320 during formation of the second polymer layer 342. Further, in some embodiments, the first end 336 of the rod 332 may be wider than the sensor 320. And in at least one such embodiment, the second end 338 of the rod 332 may be wider than the first end 336 of the rod 332.

The first end 336 of the rod 332 may take various different forms in various different embodiments. For instance, in some embodiments, the first end 336 of the rod 332 may include a complaint material. As examples, the complaint material may include a polymer, such as silicone, polyethylene terephthalate (PET), polypropylene, polyurethane, and silicone rubber. In some situations, when the complaint material includes a polymer, the polymer may be fully cured. Moreover, in at least one such embodiment, the complaint material may fully cover the sensor 320 during formation of the second polymer layer 342. Further, in some embodiments, the first end 336 of the rod 332 may have a dimension (e.g., length) between 200 micrometers to 2 millimeters. In addition, the first end 336 of the rod 332 may have a variety of shapes, such as a square, a square with rounded corners, a rectangular, a rectangular with rounded corners, and/or triangular.

Further, the rod 332 may take various different forms in various different embodiments. For instance, the rod 332 may include various different materials, such as one or more of: aluminum, Teflon, Delron, AlTiN and any other non-stick material. In some situations, when the rod 332 includes aluminum, the aluminum may be coated with Teflon or any other non-stick material. In a further aspect, the rod 334 may include a complaint material, such as silicone rubber. Moreover, in some embodiments, the rod 332 may have a first dimension (e.g., a length) between 5 to 15 millimeters. And, in some embodiments, the rod 332 may have a second dimension (e.g., a diameter) between 500 micrometers to 1.5 millimeters, such as less than 1 millimeter.

Further still, the spring 334 may take various different forms in various different embodiments. For instance, the spring 334 may include various different materials, such as a metal (e.g., stainless steel) and a polymer (e.g., elastomer). Moreover, in some embodiments, the spring 334 may be a compression spring.

In an example, when the structure 314 includes the opening 324, the rod 332 may have a dimension (e.g., first or second dimension) that is less than a respective dimension of the opening 324. With this arrangement, at least a portion of the rod 332 may be surrounded by the opening 324 during formation of the second polymer layer 342.

1. Providing a Polymer Material on the Surface of the Molding Piece

As mentioned above, at block 202, a polymer material may be provided on the surface of the molding piece. FIG. 3e illustrates an example in which a polymer material 340 is provided on the surface 328 of the third molding piece 326.

In an example, the polymer material 340 can take the form of or be similar in form to the polymer material 306. However, in other examples, the polymer material 340 may be a different polymer material than the polymer material 306. The polymer material 340 can include any of the polymer materials mentioned herein.

As shown in FIG. 3e, providing the polymer material 340 on the surface 328 of the third molding piece 326 may involve providing the polymer material 340 on the surface 328 of the third molding piece 326, such that the first end 336 of the rod 332 is located above the polymer material 340. In an example, the polymer material 340 may be provided on the surface 328 by filling the third molding piece 326 with the polymer material 340. Further, in an example, the first end 336 of the rod 332 may be located above the polymer material 340 a distance 350. And in at least one such example, the distance 350 may be around 5 millimeters. Other values for the distance 350 are possible as well.

The distance 350 may be specified in various ways. For example, the distance 350 may be specified as a distance between a highest point of the first end 336 of the rod 332 and a highest point of the polymer material 340. As another example, the distance 350 may be specified as a distance between a closest point of the first end 336 of the rod 332 and a closet point of the polymer material 340. As still another example, the distance 350 may be specified as a distance between a vertical center point of the first end 336 of the rod 332 and a vertical center point of the polymer material 340. Other examples of specifying the distance 350 are possible.

2. Orienting an Additional Molding Piece Over the Polymer Material on the Surface of the Molding Piece As mentioned above, at block 204, an additional molding piece may be oriented over the polymer material on the surface of the molding piece. FIG. 3f illustrates the fabrication device 300 orienting an additional molding piece over the polymer material on the surface of a molding piece. In particular, FIG. 3f illustrates the fabrication device 300 orienting the first molding piece 302 over the polymer material 340 on the surface 328 of the third molding piece 326. Thus, in some embodiments, the additional molding piece of the method 200 may take the form of or be similar in form to the first molding piece 302.

As shown in FIG. 3f, the first molding piece 302 may hold the structure 314 positioned on the first polymer layer 308. With this arrangement, orienting the first molding piece 302 over the polymer material 340 on the surface 328 of the third molding piece 326 may position the sensor 320 directly above the protrusion 332.

The first molding piece 302 may be oriented over the polymer material 340 on the surface 328 of the third molding piece 326 in a variety of ways. As one example, the positioning apparatus described with reference to block 104 may be further configured to orient the first molding piece 302 over the polymer 340 on the surface 328 of the third molding piece 326. For instance, the positioning system may orient the first molding piece 302 over the polymer material 340 on the surface 328 of the third molding piece 326. With this arrangement, the positioning system may position the sensor 320 directly above the protrusion 330.

In addition, the vision system of the positioning system may be further configured to assist with orienting the first molding piece 302 over the polymer material 340 on the surface 328 of the molding piece. With this arrangement, the vision system may facilitate guiding the first molding piece 302 to a precise location over the polymer material 340 on the surface 328 of third molding piece 326.

In some embodiments, the third molding piece 326 and the first molding piece 302 may be transparent, such that the sensor 320 may be visible during orienting the first molding piece 320 over the polymer 340 on the surface 328 of the third molding piece. Such an arrangement may assist in positioning the sensor 320 directly above the protrusion 330.

As another example, the fabrication device 300 may further include one or more alignment pins (not shown), such as a plurality of dowel pins, for orienting the first molding piece 302 over the polymer material 340 on the surface 328 of the third molding piece 326. The one or more alignment pins may assist in positioning the sensor 320 directly above the protrusion 330. Other ways of orienting the first molding piece 302 over the polymer material 340 on the surface 328 of the third molding piece 326 are possible as well.

Further, the first molding piece 302 may be oriented over the polymer material 340 on the surface 328 of the third molding piece 326 when a surface of the first molding piece 302 is located a distance 352 above the surface 328 of the third molding piece 326. With this arrangement, the sensor 320 may be positioned directly above the protrusion 330 when the surface of the first molding piece is located the distance 352 above the surface 328 of the third molding piece 326. In an example, the distance 352 may be 5 millimeters. Other values of the distance 352 are possible as well.

The distance 352 may be specified in various ways. For example, the distance 352 may be specified as a distance between a highest point of the surface of the first molding piece 302 and a highest point of the surface 328 of the third molding piece 326. As another example, the distance 352 may be specified as a distance between a closest point of the surface of the first molding piece 302 and a closet point of the surface 328 of the third molding piece 326. As still another example, the distance 352 may be specified as a distance between a vertical center point of the surface of the first molding piece 302 and a vertical center point of the surface 328 of the third molding piece 326. Other examples of specifying the distance 352 are possible.

3. Bringing the Molding Piece and the Oriented Additional Molding Piece Together into a Forming Position As mentioned above, at block 206, the molding piece and the oriented additional molding piece may be brought together into the forming position. FIG. 3g illustrates an example in which the fabrication device 300 brings the molding piece and the oriented additional molding piece together into the forming position. In particular, FIG. 3g illustrates the fabrication device 300 bringing the first molding piece 302 (oriented as shown in FIG. 3f) and the third molding piece 326 together into the forming position.

As shown in FIG. 3g, in the forming position (i) the polymer material 340 on the surface 330 of the third molding piece 326 may contact the structure 314 and the first polymer layer 308 held by the first molding piece 302 and (ii) the sensor 320 contacts the protrusion 330. In this forming position, there may be a boundary 341 between the first polymer layer 308 and the polymer material 340. And in this forming position, the polymer material 340 may be cured to form the second polymer layer 342.

Moreover, as shown in FIG. 3g, the protrusion 330 extends from the surface 328 of the third molding piece 326 to the sensor 320 through the polymer material 340 as the second polymer layer 342 is being formed. With this arrangement, the protrusion 330 may block the second polymer layer 342 from molding over the sensor 320. As a result, the second polymer layer 342 may mold over the structure 314, such that the structure 314 is fully enclosed by the first polymer layer 308, the second polymer layer 342, and the protrusion 330.

Further, as shown in FIG. 3g, the first end 336 of the rod 332 and a different portion of the rod 332 may be surrounded by the polymer material 340 during formation of the second polymer layer 342. However, in other examples, the different portion of the rod 332 might not be surrounded by the polymer material 340 during formation of the second polymer layer 342. Instead, in some such examples, the first end 336 of the rod 332 may be surrounded by the polymer material 340 during formation of the second polymer layer 342.

As noted, in the forming position, there may be the boundary 341 between the first polymer layer 308 and the polymer material 340. In an example, the rod 332 may be moveable and bringing the third molding piece 326 and the first molding piece 302 together into the forming position may move the rod 332 downward such that a portion of the first end 336 of the rod 332 is substantially flush with a surface of the polymer material 340. The term "substantially flush," as used in this disclosure, refers to exactly flush with a surface of the polymer 340 defined by the boundary 341 or one or more deviations from exactly flush with the surface that do not significantly impact forming a channel through a polymer layer as described herein.

As noted, the spring 334 may be configured to press the first end 336 of the rod 332 against the sensor 320 during formation of the second polymer layer 342. In some embodiments, the spring 334 may be further configured to deform a distance 354 when pressing the first end 336 of the rod 332 against the sensor 320 during formation of the second polymer layer 342. And in at least one such embodiment, the distance 354 may be between 0.5 to 10 millimeters, such as between 0.5 to 2 millimeters or between 5 to 10 millimeters. Other values for the distance 354 are possible as well. Further, in at least one such embodiment, the distance 354 may be greater than a thickness of the polymer material 340. The distance 354 may be referred to as spring travel.

Moreover, in some embodiments, the spring 334 may be loaded when pressing the first end 336 of the rod 332 against the sensor 320 during formation of the second polymer layer 342. In an example, the load on the spring 334 may be less than 5 pounds. Other values for the load on the spring 334 are possible as well.

The first molding piece 302 and the third molding piece 326 may be configured to achieve a given desired thickness of a layer formed between the two molding pieces. As one example, the first molding piece 302 and the third molding piece 326 may be designed so as to define a thickness of the second polymer layer 342. As another example, the first molding piece 302 and the third molding piece 326 may be designed so as to define a final thickness of an eye-mountable device, such as the eye-mountable device 400. In an example, the first molding piece 302 and the third molding piece 326 can be designed so as to allow for a layer having a given desired thickness between the two pieces (in addition to a thickness of the first polymer 308). As such, when the first molding piece 302 and the third molding piece 326 are pressed together during formation of a layer, the resulting layer will have the given desired thickness.

In an example, the second polymer layer 342 has a thickness of greater than 50 micrometers. However, in other examples, the second polymer layer 342 can have a thickness between 50 and 300 micrometers, such as 130 micrometers. It should be understood that since the second polymer layer 342 may mold over the structure 314 except for the sensor 320, the second polymer layer 342 may not have a uniform thickness. For instance, the thickness of the second polymer layer 342 above the electronics 322 may be less than the thickness of the second polymer layer 342 that is not touching the electronics 322.

In some embodiments, the second polymer layer 342 can be thicker than the first polymer layer 308.

In an example, the thickness of the second polymer layer 342 can be selected based on a particular analyte or analytes that the eye-mountable device, such as the eye-mountable device 400, is configured to detect. For example, an optimal thickness for a first analyte may be 10 micrometers, while an optimal thickness for a second analyte may be 25 micrometers. Other examples are possible as well.

As noted, the polymer material 340 can take the form of or be similar in form to the polymer material 306. As a result, the second polymer layer 342 can be composed of the same or similar polymer material as the first polymer layer 308. However, in other examples, the second polymer layer 342 can be composed of a different polymer material than the first polymer layer 308. In an example, the structure 314 can be more rigid than the second polymer layer 342.

The second polymer layer 342 defines an anterior side (or a second side) 344 of an eye-mountable device. That is, the second polymer layer 342 defines an outer edge of the eye-mountable device. When mounted on an eye of a user, the anterior side 344 of the eye-mountable device defined by the second polymer layer 342 corresponds to the side of the device that is not touching the eye of the user. As shown in FIG. 3g, the anterior side 344 is opposite the posterior side 310. The third molding piece 326 may be shaped so as to define a shape of the anterior side 344. For example, a curvature of the anterior side 344 may be defined by the third molding piece 326.

4. In the Forming Position, Curing the Second Polymer Layer to Form the Second Polymer Layer As mentioned above, at block 208, in the forming position, the polymer material may be cured to form the second polymer layer. FIG. 3h illustrates an example in which the fabrication device 300 cures the polymer material to form the second polymer layer. In particular, FIG. 3h illustrates in the forming position, the fabrication device 300 curing the polymer material 340 to form the second polymer layer 342.

In an example, the curing to form the second polymer layer 342 can be similar to the curing of the first polymer layer 308. However, in other examples, the curing to form the second polymer layer 342 may involve different techniques than the curing of the first polymer layer 308. Polymer material 340 can be cured by any of the techniques mentioned herein to form second polymer layer 342. In some examples, the fabrication device 300 may also cure (or partially cure) the first polymer layer 308 at this stage.

As shown in FIG. 3h, the first end 336 of the rod 332 and a different portion of the rod 332 may be surrounded by the polymer material 340 as it is being cured to form the second polymer layer 342. However, in some examples, the different portion of the rod 332 might not be surrounded by the polymer material 340 as it is being cured to form the second polymer layer 342. Instead, in some such examples, the first end 336 of the rod 332 may be surrounded by the polymer material 340 as it is being cured to form the second polymer layer 342. After the polymer material 340 has been cured to form the second polymer layer 342, there may not be a visible boundary line (e.g., the boundary 341) separating the first polymer layer 308 from the second polymer layer 342.

D. Removing the Body-Mountable Device from the Molding Piece

As mentioned above, at block 108, the body-mountable device may be removed from the molding piece. FIG. 3i illustrates an example in which the fabrication device 300 removes an eye-mountable device 346 from the third molding piece 326.

The eye-mountable device 346 includes the first polymer layer 308, the posterior side 310, the structure 314, the sensor 320, the electronics 322, the second polymer layer 342, and the anterior side 344. In addition, as shown in FIG. 3i, the eye-mountable device 346 removed from the third molding piece 326 has a channel 348 to the sensor 320 formed by the protrusion 330. And as shown in FIG. 3h, the channel 348 is through the second polymer layer 342.

In an example, a dimension of the rod 332 may define a dimension of the channel 348. And in at least one such example, a dimension of the first end 336 of the rod 332 may define a dimension of the channel 348. For instance, when the first end 336 of the rod 332 is surrounded by the polymer material 340 during formation of the second polymer layer 342, the dimension of the first end 336 of the rod 332 may define a dimension of the channel 348. However, when the first end 336 of the rod 332 and a different portion of the rod 332 are surrounded by the polymer material 340 during formation of the second polymer layer 342, the first end 336 of the rod and the different portion of the rod 332 may define a dimension of the channel 348.

In order to remove the eye-mountable device 346 from the third molding piece 326, the fabrication device 300 may separate the first molding piece 302 from the third molding piece 326. When the fabrication device 300 separates the first molding piece 302 from the third molding piece 346, the eye-mountable device 346 may stick to a side of the first molding piece 302. As shown in FIG. 3i, with this arrangement, the first molding piece 302 can hold the eye-mountable device. In an example, the first polymer layer 308 and/or the first molding piece 302 can be surface treated, such that the eye-mountable device 346 sticks to the side of the first molding piece 302. Additionally or alternatively, the third molding piece 326 and/or the eye-mountable device 346 can be surface treated, such that the eye-mountable device 346 sticks to the side of the first molding piece 302.

After the first molding piece 302 is separated from the third molding piece 326, the eye-mountable device 346 may be removed from the first molding piece 302. In an example, removing the eye-mountable device 346 from the first molding piece 302 can include the fabrication device 300 removing the surface treatment of the eye-mountable device 346 and/or the first molding piece 302.

Figure 4:
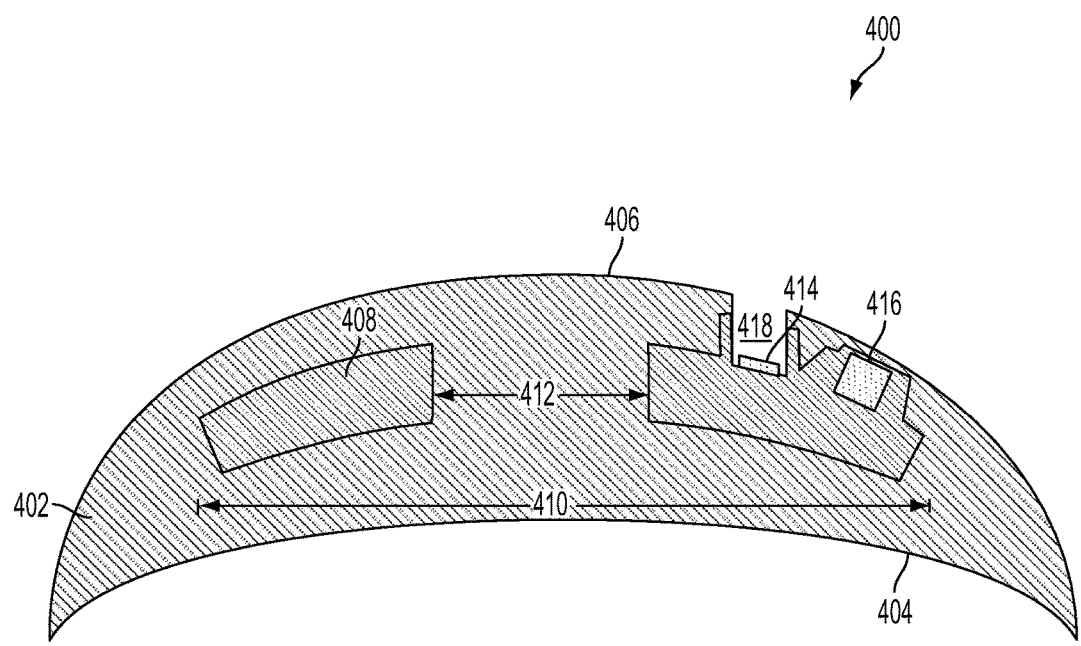
FIG. 4 is an illustration of an eye-mountable device formed according to an example embodiment.

As mentioned above, FIG. 4 illustrates the eye-mountable device 400 formed according to an example embodiment. In particular, FIG. 4 illustrates an anterior side 406 including a channel 418 to the sensor 414.

In the eye-mountable device 400, a structure 408 is embedded in the transparent polymer 402. The structure 408 has an outer diameter 410 and inner diameter 412 and includes a sensor 414 configured to detect an analyte and electronics 416. The eye-mountable device 400 includes a posterior side 404 and the anterior side 406. The transparent polymer 402 may take the form of or be similar in form to the first polymer layer 308 and the second polymer layer 342, the structure 408 may take the form of or be similar in form to the structure 314, the sensor 414 may take the form of or be similar in form to the sensor 320, and the electronics 416 may take the form of or be similar in form to the electronics 322.

In an example, the inner diameter 412 can be asymmetric and define a rotational orientation of the structure 408 relative to the channel 418, such that the sensor 314 is configured to receive the analyte via the channel 418. With this arrangement, the structure 408 is fully enclosed by the transparent polymer 402, except for the sensor 414 being exposed by the channel 418.

In some examples, one or more dimensions of the channel 418 may be based on one or more dimensions of the sensor 414 and/or the electronics 416. As one example, a width of the channel 418 can be based on a width of the sensor 414. As another example, a height of the channel 418 can be based on a height of the electronics 416.

While the body-mountable device has been described as comprising the eye-mountable device 346 and the eye-mountable device 400, the body-mountable device could comprise other mountable devices that are mounted on or in other portions of the human body.

For example, in some embodiments, the body-mountable device may comprise a tooth-mountable device. In some embodiments, the tooth-mountable device may take the form of or be similar in form to the eye-mountable device 346 and/or the eye-mountable device 400. For instance, the tooth-mountable device may include polymer layers and/or a transparent polymer that are the same or similar to any of the polymer layers and/or transparent polymers described herein and a structure that is the same or similar to any of the structures described herein. With this arrangement, the tooth-mountable device may be configured to detect at least one analyte in a fluid (e.g., saliva) of a user wearing the tooth-mountable device.

Moreover, in some embodiments, the body-mountable device may comprise a skin-mountable device. In some embodiments, the skin-mountable device may take the form of or be similar in form to the eye-mountable device 346 and/or the eye-mountable device 400. For instance, the tooth-mountable device may include polymer layers and/or a transparent polymer that are the same or similar to any of the polymer layers and/or transparent polymers described herein and a structure that is the same or similar to any of the structures described herein. With this arrangement, the skin-mountable device may be configured to detect at least one analyte in a fluid (e.g., perspiration, blood, etc.) of a user wearing the skin-mountable device.

Further, some embodiments may include privacy controls which may be automatically implemented or controlled by the wearer of a body-mountable device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a body-mountable device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

E. Applying a Non-Stick Coating to at Least One of the Rod or Sensor

The method 100 may further involve applying a non-stick coating to at least one of the sensor or the rod. In an example, applying the non-stick coating to at least one of the sensor or the rod may occur before forming the second polymer layer.

For instance, the fabrication device 300 may apply a non-stick coating to at least one of the sensor 320 or the rod 332. And in some examples, the fabrication device 300 may apply the non-stick coating to at least one of the sensor 320 or the rod 332 before formation of the second polymer layer 342. With this arrangement, the rod 332 may not stick to the sensor 320, the first polymer layer 308, and/or the second polymer layer 342 during formation of the second polymer layer. As examples, the non-stick coating may include one or more of: an oil, grease, a surfactant, and silane. Further, in some examples, the rod 332 may not bond to the first polymer layer 308 and/or the second polymer layer 342 during formation of the second polymer layer 342.

In an example, the non-stick coating may be applied to the first end 336 of the rod 332. In other examples, the non-stick coating may be applied to a portion of the rod 332. And in yet other examples, the non-stick coating may be applied to the first end 336 of the rod 332 and the portion of the rod 332.

In a further aspect, when the rod 332 includes a compliant material, an oil and/or grease may be applied to a portion of the rod 332. With this arrangement, the rod 332 may not stick to the sensor 320, the first polymer layer 308, and/or the second polymer layer 342 during formation of the second polymer layer 342.

III. Example Apparatus, Systems, and Devices

A. Example Apparatus

As mentioned above, a body-mountable device may be formed using example methods described above. Apparatus for forming a body-mountable device is described in greater detail below.

The body-mountable device formed by the apparatus described herein may include a first polymer layer defining a first side of the body-mountable device, a second polymer layer defining a second side of the body-mountable device, and a structure including a sensor between the first and second polymer layers.

The first polymer layer could take the form of or be similar in form to the first polymer layer 308, the first side of the body-mountable device could take the form of or be similar in form to the posterior side 310, the second polymer layer could take the form of or be similar in form to the second polymer layer 342, the second side of the body-mountable device could take the form of or be similar in form to the anterior side 344, the structure could take the form of or be similar in form to the structure 314, and the sensor could take the form of or be similar in for to the sensor 320.

Figure 5:
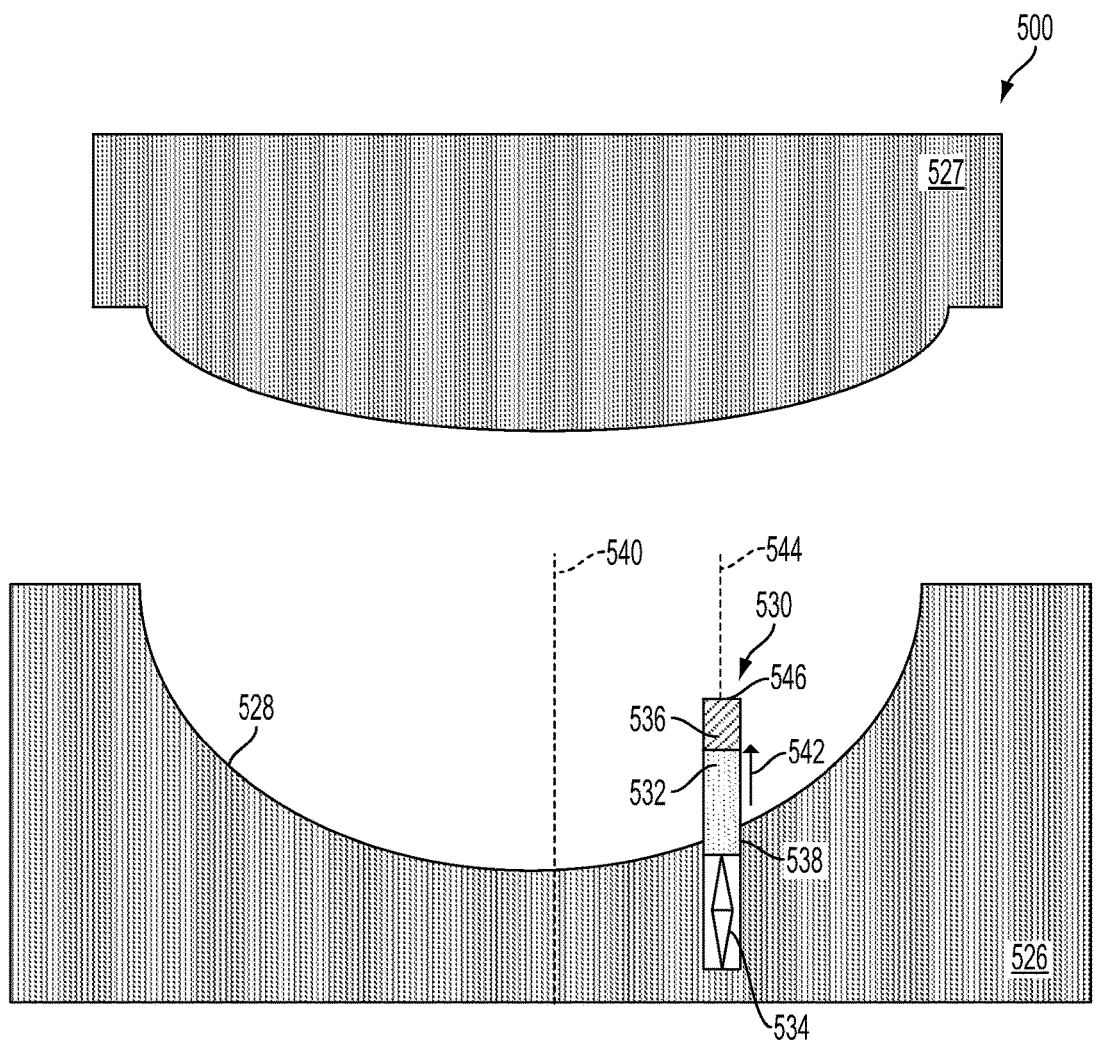
FIG. 5 is an illustration of an apparatus for forming a body-mountable device, according to an example embodiment.

FIG. 5 illustrates an apparatus 500 for forming a body-mountable device, according to an example embodiment. As shown in FIG. 5, the apparatus 500 includes a first molding piece 526 and a second molding piece 527.

The first molding piece 526 includes a surface 528 configured to support the second polymer layer as the second polymer layer is being formed and a protrusion 530 that extends from the surface 528. The second molding piece 527 may be configured to hold the first polymer layer and the structure against the second polymer layer as the second polymer layer is being formed, such that the protrusion 530 contacts the sensor as the second polymer layer is being formed.

The first molding piece 526 may take the form of or be similar in form to the third molding piece 326, the second molding piece 527 may take the form of or be similar in form to the first molding piece 302, the surface 528 may take the form of or be similar in form to the surface 328, and the protrusion 530 may take the form of or be similar in form to the protrusion 330.

In another aspect, the surface 528 of the first molding piece 526 may be substantially symmetric about an axis 540. With this arrangement, the protrusion 530 may extend from the surface 528 in a direction 542 that is substantially parallel to the axis 540.

The term "substantially symmetric," as used in this disclosure, refers to exactly symmetric or one or more deviations from exactly symmetric that do not significantly impact forming a channel through a polymer layer using a protrusion as described herein. Further, the term "substantially parallel," as used in this disclosure, refers to exactly parallel or one or more deviations from exactly parallel that do not significantly impact forming a channel through a polymer layer using a protrusion as described herein.

In an example, the protrusion 530 may include a rod 532 and a spring 534. The rod 532 may include a first end 536 and a second end 538, and the spring 534 may be connected to second end 538 and configured to press the first end 536 of the rod 532 against the sensor during formation of the second polymer layer.

The rod 532 may take the form of or be similar in form to the rod 332, the spring 534 may take the form of or be similar in form to the spring 334, the first end 536 of the rod 532 may take the form of or be similar in form to the first end 336 of the rod 332, and the second end 538 of the rod 532 may take the form of or be similar in form to the second end 338 of the rod 332. For instance, in an example, the first end 536 of the rod 532 may include a complaint material.

In further aspect, the rod 332 may include an axis 544 and the first end 536 of the rod 532 may include a surface 546 that is substantially perpendicular to the axis 544 of the rod 532. The term "substantially perpendicular," as used in this disclosure, refers to exactly perpendicular or one or more deviations from exactly perpendicular that do not significantly impact forming a channel through a polymer layer using a protrusion as described herein.

Figure 6:
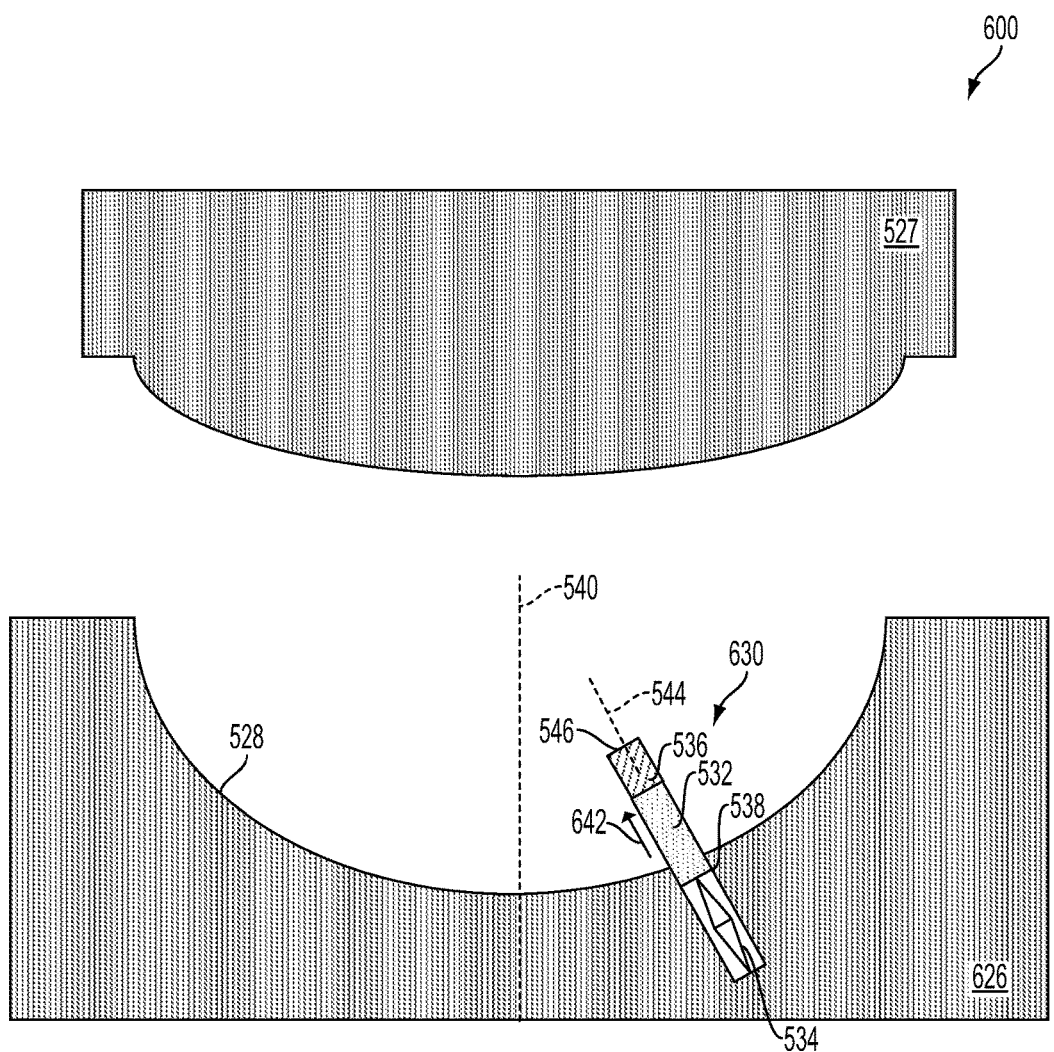
FIG. 6 is an illustration of another apparatus for forming a body-mountable device, according to an example embodiment.

FIG. 6 illustrates another apparatus 600 for forming a body-mountable device, according to an example embodiment. As shown in FIG. 6, the apparatus 600 includes a protrusion 630 that extends from the surface 528 of a first molding piece 626 in a direction 642 that is non-parallel to the axis 540 of the first molding piece 626.

The apparatus 600 includes the first molding piece 626 and the second molding piece 527. The first molding piece includes 626 includes the surface 528 configured to support the second polymer layer as the second polymer layer is being formed and the protrusion 630 that extends from the surface 528. The second molding piece 527 may be configured to hold the first polymer layer and the structure against the second polymer layer as the second polymer layer is being formed, such that the protrusion 630 contacts the sensor as the second polymer layer is being formed.

In another aspect, the surface 528 of the first molding piece 626 may be substantially symmetric about the axis 540. As noted, the protrusion may extend from the surface 528 in the direction 642 that is non-parallel to the axis 540.

In an example, the protrusion 630 may include a rod 532 and a spring 534. The rod 532 may include a first end 536 and a second end 538, and the spring 534 may be connected to second end 538 and configured to press the first end 536 of the rod 532 against the sensor during formation of the second polymer layer.

In a further aspect, the rod 532 may include the axis 544 and the first end 536 of the rod 532 may include the surface 546 that is substantially perpendicular to the axis 544 of the rod 532.

Figure 7:
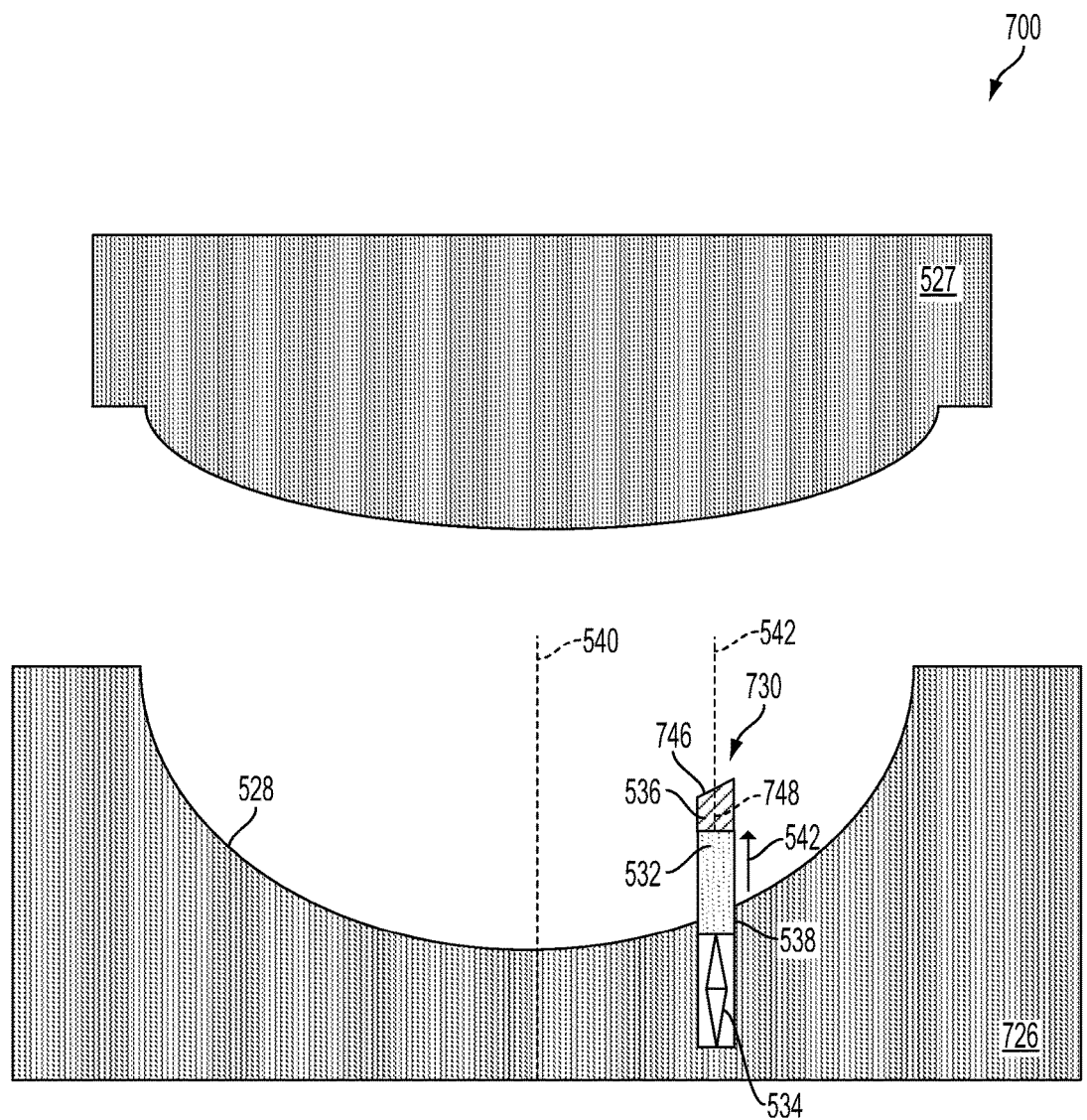
FIG. 7 is an illustration of yet another apparatus for forming a body-mountable device, according to an example embodiment.

FIG. 7 illustrates yet another apparatus 700 for forming a body-mountable device, according to an example embodiment. As shown in FIG. 7, the apparatus 700 includes a surface 746 of the first end 536 of the rod 532 that is at a non-perpendicular angle 748 from the axis 542 of the rod 532.

The apparatus 700 includes a first molding piece 726 and the second molding piece 527. The first molding piece includes 726 includes the surface 528 configured to support the second polymer layer as the second polymer layer is being formed and a protrusion 730 that extends from the surface 528. The second molding piece 527 may be configured to hold the first polymer layer and the structure against the second polymer layer as the second polymer layer is being formed, such that the protrusion 730 contacts the sensor as the second polymer layer is being formed.

In another aspect, the surface 528 of the first molding piece 726 may be substantially symmetric about the axis 540 of the first molding piece 726. With this arrangement, the protrusion 730 may extend from the surface 528 in the direction 542 that is substantially parallel to the axis 540.

In an example, the protrusion 730 may include a rod 532 and a spring 534. The rod 532 may include a first end 536 and a second end 538, and the spring 534 may be connected to second end 538 and configured to press the first end 536 of the rod 532 against the sensor during formation of the second polymer layer.

In a further aspect, the rod 532 may include the axis 544 and, as noted, the first end 536 of the rod 532 may include the surface 746 that is at the non-perpendicular angle 748 to the axis 544 of the rod 532.

When a body-mountable device that includes a sensor is formed by the apparatus 500, the apparatus 600, and/or the apparatus 700, the body-mountable device may include a channel (or a molded channel) to the sensor. The channel may take the form of or be similar in form to the channel 348 and/or the channel 418. For instance, at least one dimension of the channel may be based on a respective dimension of the sensor.

While the protrusion 330, the protrusion 530, the protrusion 630, and protrusion 730 have been described as including a rod and a spring, in some examples a protrusion might not include a rod and spring. For instance, the protrusion may include a complaint material. With this arrangement, the protrusion may be configured to deform a certain distance when pressing an end of the protrusion against a sensor (e.g., the sensor 320) during formation of a second polymer layer (e.g., the second polymer layer 342).

As another example, the protrusion may include a non-compliant material. With this arrangement, the protrusion may be configured to remain substantially stationary when pressing an end of the protrusion against the sensor during formation of a second polymer layer. The term "substantially stationary," as used in this disclosure, may refer to exactly stationary or one or more deviations from exactly stationary that do not significantly impact forming a channel through a polymer layer using a protrusion as described herein.

B. Example System and Devices

As mentioned above, a body-mountable device may be formed using the example methods described above. Further, the body-mountable device may be configured to monitor health-related information based on at least one analyte detected in a fluid of a user wearing the body-mountable device. An eye-mountable device configured to monitor health-related information based on at least one analyte detected from an eye of a user is described in greater detail below with reference to FIGS. 8 and 9a-d.

A structure in accordance with an exemplary embodiment may include a sensor, electronics, and an antenna all situated on a substrate. The electronics may operate the sensor to perform readings and operate the antenna to wirelessly communicate the readings from the sensor to an external reader via the antenna. The sensor can be arranged on the substrate to face outward, away from the corneal surface of the user, so as to generate clinically relevant readings from tear fluid of the user that the sensor receives via a channel in the anterior side of the eye-mountable device. For example, the sensor can be suspended in the lens material and situated such that the sensor is less than 10 micrometers from the anterior edge of the eye-mountable device. The sensor can generate an output signal indicative of a concentration of an analyte that the sensor receives via the channel.

Figure 8:
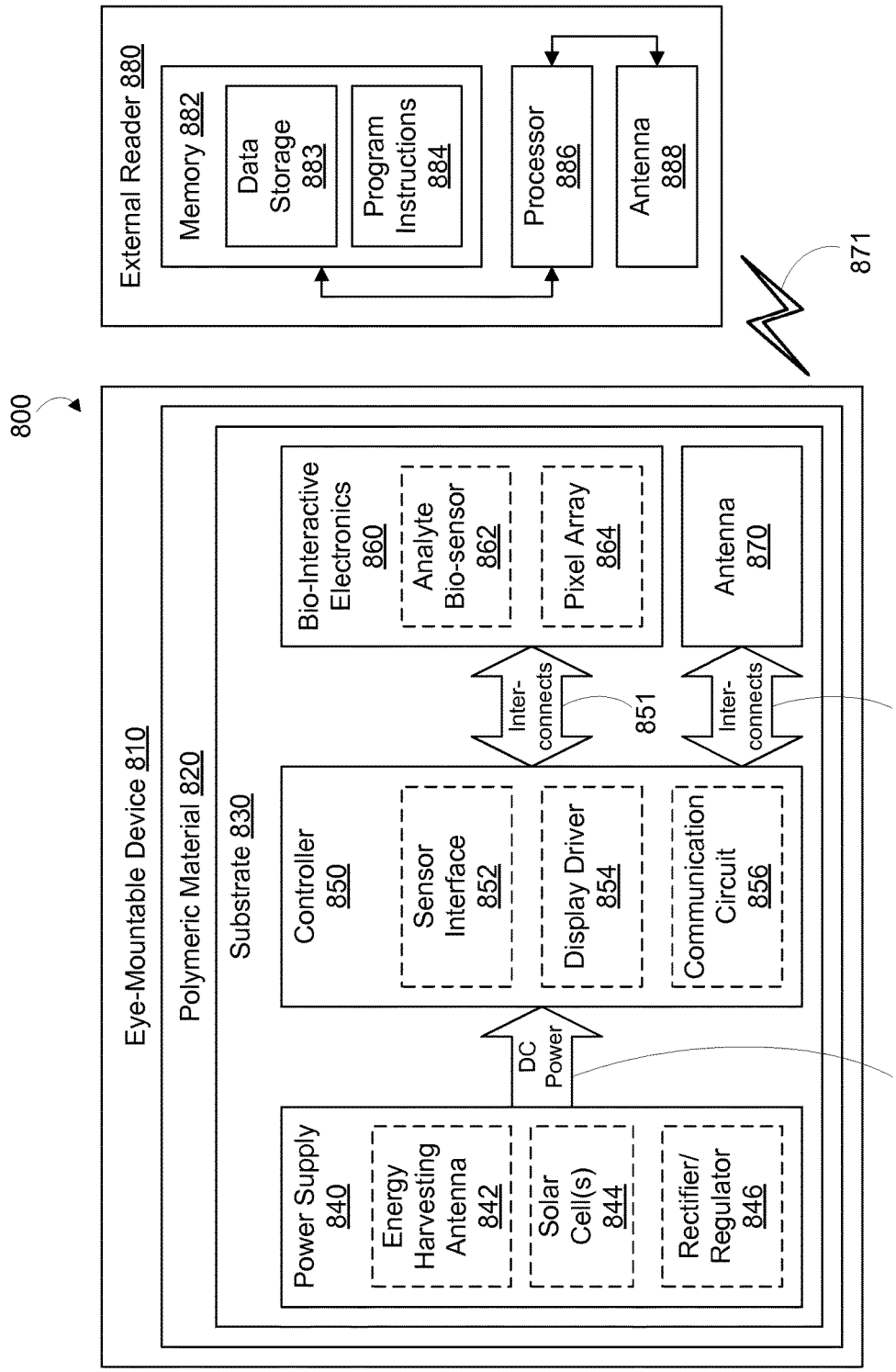
FIG. 8 is a block diagram of a system with an eye-mountable device in wireless communication with an external reader, according to an example embodiment.

FIG. 8 is a block diagram of a system 800 with an eye-mountable device 810 in wireless communication with an external reader 880. The exposed regions of the eye-mountable device 810 are made of a polymeric material 820 formed to be contact-mounted to a corneal surface of an eye. In accordance with the exemplary methods, polymeric material 820 may comprise a first polymer layer and a second polymer layer.

Substrate 830 is embedded in the polymeric material 820 to provide a mounting surface for a power supply 840, a controller 850, bio-interactive electronics 860, and an antenna 870. The bio-interactive electronics 860 are operated by the controller 850. The power supply 840 supplies operating voltages to the controller 850 and/or the bio-interactive electronics 860. The antenna 870 is operated by the controller 850 to communicate information to and/or from the eye-mountable device 810. The antenna 870, the controller 850, the power supply 840, and the bio-interactive electronics 860 can all be situated on the embedded substrate 830. Because the eye-mountable device 810 includes electronics and is configured to be contact-mounted to an eye, it may also be referred to as an ophthalmic electronics platform.

To facilitate contact-mounting, the polymeric material 820 can have a concave surface configured to adhere ("mount") to a moistened corneal surface (e.g., by capillary forces with a tear film coating the corneal surface). Additionally or alternatively, the eye-mountable device 810 can be adhered by a vacuum force between the corneal surface and the polymeric material due to the concave curvature. While mounted with the concave surface against the eye, the anterior or outward-facing surface of the polymeric material 820 can have a convex curvature that is formed to not interfere with eye-lid motion while the eye-mountable device 810 is mounted to the eye. For example, the polymeric material 820 can be a substantially transparent curved polymeric disk shaped similarly to a contact lens.

The polymeric material 820 can include one or more biocompatible materials, such as those employed for use in contact lenses or other ophthalmic applications involving direct contact with the corneal surface. The polymeric material 820 can optionally be formed in part from such biocompatible materials or can include an outer coating with such biocompatible materials. The polymeric material 820 can include materials configured to moisturize the corneal surface, such as hydrogels and the like. In some instances, the polymeric material 820 can be a deformable ("non-rigid") material to enhance wearer comfort. In some instances, the polymeric material 820 can be shaped to provide a predetermined, vision-correcting optical power, such as can be provided by a contact lens.

The substrate 830 includes one or more surfaces suitable for mounting the bio-interactive electronics 860, the controller 850, the power supply 840, and the antenna 870. The substrate 830 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, substantially transparent conductive materials (e.g., indium tin oxide) can be patterned on the substrate 830 to form circuitry, electrodes, etc. For example, the antenna 870 can be formed by depositing a pattern of gold or another conductive material on the substrate 830. Similarly, interconnects 851, 857 between the controller 850 and the bio-interactive electronics 860, and between the controller 850 and the antenna 870, respectively, can be formed by depositing suitable patterns of conductive materials on the substrate 830. A combination of resists, masks, and deposition techniques can be employed to pattern materials on the substrate 830.

The substrate 830 can be a relatively rigid polymeric material, such as PET, paralyene or another material sufficient to structurally support the circuitry and/or electronics within the polymeric material 820. The eye-mountable device 810 can alternatively be arranged with a group of unconnected substrates rather than a single substrate. For example, the controller 850 and a bio-sensor or other bio-interactive electronic component can be mounted to one substrate, while the antenna 870 is mounted to another substrate and the two can be electrically connected via the interconnects 857.

In some embodiments, the bio-interactive electronics 860 (and the substrate 830) can be positioned away from the center of the eye-mountable device 810 and thereby avoid interference with light transmission to the eye through the center of the eye-mountable device 810. For example, where the eye-mountable device 810 is shaped as a concave-curved disk, the substrate 830 can be embedded around the periphery (e.g., near the outer circumference) of the disk. In some embodiments, the bio-interactive electronics 860 (and the substrate 830) can be positioned in the center region of the eye-mountable device 810. The bio-interactive electronics 860 and/or the substrate 830 can be substantially transparent to incoming visible light to mitigate interference with light transmission to the eye. Moreover, in some embodiments, the bio-interactive electronics 860 can include a pixel array 864 that emits and/or transmits light to be perceived by the eye according to display driver instructions. Thus, the bio-interactive electronics 860 can optionally be positioned in the center of the eye-mountable device so as to generate perceivable visual cues to a wearer of the eye-mountable device 810, such as by displaying information via the pixel array 864.

The substrate 830 can be shaped as a flattened ring with a radial width dimension sufficient to provide a mounting platform for the embedded electronics components. The substrate 830 can have a thickness sufficiently small to allow the substrate 830 to be embedded in the polymeric material 820 without influencing the profile of the eye-mountable device 810. The substrate 830 can have a thickness sufficiently large to provide structural stability suitable for supporting the electronics mounted thereon. For example, the substrate 830 can be shaped as a ring with a diameter of about 10 millimeters, a radial width of about 1 millimeter (e.g., an outer radius 1 millimeter larger than an inner radius), and a thickness of about 50 micrometers. The substrate 830 can optionally be aligned with the curvature of the anterior side of the eye-mountable device.

The power supply 840 is configured to harvest ambient energy to power the controller 850 and bio-interactive electronics 860. For example, a radio-frequency energy harvesting antenna 842 can capture energy from incident radio radiation. Additionally or alternatively, solar cell(s) 844 ("photovoltaic cells") can capture energy from incoming ultraviolet, visible, and/or infrared radiation. Furthermore, an inertial power scavenging system can be included to capture energy from ambient vibrations. The energy harvesting antenna 842 can optionally be a dual-purpose antenna that is also used to communicate information to the external reader 880. That is, the functions of the antenna 870 and the energy harvesting antenna 842 can be accomplished with the same physical antenna.

A rectifier/regulator 846 can be used to condition the captured energy to a stable DC supply voltage 841 that is supplied to the controller 850. For example, the energy harvesting antenna 842 can receive incident radio frequency radiation. Varying electrical signals on the leads of the antenna 842 are output to the rectifier/regulator 846. The rectifier/regulator 846 rectifies the varying electrical signals to a DC voltage and regulates the rectified DC voltage to a level suitable for operating the controller 850. Additionally or alternatively, output voltage from the solar cell(s) 844 can be regulated to a level suitable for operating the controller 850. The rectifier/regulator 846 can include one or more energy storage devices arranged to mitigate high frequency variations in the ambient energy harvesting antenna 842 and/or solar cell(s) 844. For example, an energy storage device (e.g., capacitor, inductor, etc.) can be connected to the output of the rectifier/regulator 846 so as to function as a low-pass filter.

The controller 850 is turned on when the DC supply voltage 841 is provided to the controller 850, and the logic in the controller 850 operates the bio-interactive electronics 860 and the antenna 870. The controller 850 can include logic circuitry configured to operate the bio-interactive electronics 860 so as to interact with a biological environment of the eye-mountable device 810. The interaction could involve the use of one or more components, such as an analyte bio-sensor 862, in bio-interactive electronics 860 to obtain input from the biological environment. Alternatively or additionally, the interaction could involve the use of one or more components, such as the pixel array 864, to provide an output to the biological environment.

In one example, a sensor interface module 852 can be included for operating the analyte bio-sensor 862. The analyte bio-sensor 862 can be, for example, an amperometric electrochemical sensor that includes a working electrode and a reference electrode. Application of an appropriate voltage between the working and reference electrodes can cause an analyte to undergo electrochemical reactions (e.g., reduction and/or oxidation reactions) at the working electrode to generate an amperometric current. The amperometric current can be dependent on the analyte concentration, and thus the amount of amperometric current can provide an indication of analyte concentration. In some embodiments, the sensor interface module 852 can be a potentiostat configured to apply a voltage difference between the working and reference electrodes while measuring a current through the working electrode.

In some instances, a reagent can also be included to sensitize the electrochemical sensor to desired analytes. For example, a layer of glucose oxidase ("GOD") can be situated around the working electrode to catalyze glucose into hydrogen peroxide ($H_2O_2$). The hydrogen peroxide can then be oxidized at the working electrode, which releases electrons to the working electrode, which generates a current.

$$\text{glucose} + O_2 \xrightarrow{GOD} H_2O_2 + \text{gluconolactone}$$
$$H_2O_2 \rightarrow 2H^+ + O_2 + 2e^-$$

The current generated by either reduction or oxidation reactions can be approximately proportionate to the reaction rate. Further, the reaction rate can be dependent on the rate of analyte molecules reaching the electrochemical sensor electrodes to fuel the reduction or oxidation reactions, either directly or catalytically through a reagent. In a steady state, where analyte molecules diffuse to the electrochemical sensor electrodes from a sampled region at approximately the same rate that additional analyte molecules diffuse to the sampled region from surrounding regions, the reaction rate can be approximately proportionate to the concentration of the analyte molecules. The current can thus provide an indication of the analyte concentration.

The controller 850 can optionally include a display driver module 854 for operating the pixel array 864. The pixel array 864 can be an array of separately programmable light transmitting, light reflecting, and/or light emitting pixels arranged in rows and columns. The individual pixel circuits can optionally include liquid crystal technologies, microelectromechanical technologies, emissive diode technologies, etc. to selectively transmit, reflect, and/or emit light according to information from the display driver module 854. Such a pixel array 864 can also optionally include more than one color of pixels (e.g., red, green, and blue pixels) to render visual content in color. The display driver module 854 can include, for example, one or more data lines providing programming information to the separately programmed pixels in the pixel array 864 and one or more addressing lines for setting groups of pixels to receive such programming information. Such a pixel array 864 situated on the eye can also include one or more lenses to direct light from the pixel array to a focal plane perceivable by the eye.

The controller 850 can also include a communication circuit 856 for sending and/or receiving information via the antenna 870. The communication circuit 856 can optionally include one or more oscillators, mixers, frequency injectors, etc. to modulate and/or demodulate information on a carrier frequency to be transmitted and/or received by the antenna 870. In some examples, the eye-mountable device 810 is configured to indicate an output from a bio-sensor by modulating an impedance of the antenna 870 in a manner that is perceivable by the external reader 880. For example, the communication circuit 856 can cause variations in the amplitude, phase, and/or frequency of backscatter radiation from the antenna 870, and such variations can be detected by the external reader 880.

The controller 850 is connected to the bio-interactive electronics 860 via interconnects 851. For example, where the controller 850 includes logic elements implemented in an integrated circuit to form the sensor interface module 852 and/or display driver module 854, a patterned conductive material (e.g., gold, platinum, palladium, titanium, copper, aluminum, silver, metals, combinations of these, etc.) can connect a terminal on the chip to the bio-interactive electronics 860. Similarly, the controller 850 is connected to the antenna 870 via interconnects 857.

It is noted that the block diagram shown in FIG. 8 is described in connection with functional modules for convenience in description. However, embodiments of the eye-mountable device 810 can be arranged with one or more of the functional modules ("sub-systems") implemented in a single chip, integrated circuit, and/or physical feature. For example, while the rectifier/regulator 846 is illustrated in the power supply block 840, the rectifier/regulator 846 can be implemented in a chip that also includes the logic elements of the controller 850 and/or other features of the embedded electronics in the eye-mountable device 810. Thus, the DC supply voltage 841 that is provided to the controller 850 from the power supply 840 can be a supply voltage that is provided on a chip by rectifier and/or regulator components of the same chip. That is, the functional blocks in FIG. 8 shown as the power supply block 840 and controller block 850 need not be implemented as separated modules. Moreover, one or more of the functional modules described in FIG. 8 can be implemented by separately packaged chips electrically connected to one another.

Additionally or alternatively, the energy harvesting antenna 842 and the antenna 870 can be implemented with the same physical antenna. For example, a loop antenna can both harvest incident radiation for power generation and communicate information via backscatter radiation.

The external reader 880 includes an antenna 888 (or group of more than one antennae) to send and receive wireless signals 871 to and from the eye-mountable device 810. The external reader 880 also includes a computing system with a processor 886 in communication with a memory 882. The memory 882 is a non-transitory computer-readable medium that can include, without limitation, magnetic disks, optical disks, organic memory, and/or any other volatile (e.g., RAM) or non-volatile (e.g., ROM) storage system readable by the processor 886. The memory 882 can include a data storage 883 to store indications of data structures, such as sensor readings (e.g., from the analyte bio-sensor 862), program settings (e.g., to adjust behavior of the eye-mountable device 810 and/or external reader 880), etc. The memory can also include program instructions 884 for execution by the processor 886 to cause the external reader to perform processes specified by the program instructions 884. For example, the program instructions 884 can cause external reader 880 to provide a user interface that allows for retrieving information communicated from the eye-mountable device 810 (e.g., sensor outputs from the analyte bio-sensor 862). The external reader 880 can also include one or more hardware components for operating the antenna 888 to send and receive the wireless signals 871 to and from the eye-mountable device 810. For example, oscillators, frequency injectors, encoders, decoders, amplifiers, filters, etc. can drive the antenna 888 according to instructions from the processor 886.

The external reader 880 can be a smart phone, digital assistant, or other portable computing device with wireless connectivity sufficient to provide the wireless communication link 871. The external reader 880 can also be implemented as an antenna module that can be plugged in to a portable computing device, such as in an example where the communication link 871 operates at carrier frequencies not commonly employed in portable computing devices. In some instances, the external reader 880 is a special-purpose device configured to be worn relatively near a wearer's eye to allow the wireless communication link 871 to operate with a low power budget. For example, the external reader 880 can be integrated in a piece of jewelry such as a necklace, earring, etc. or integrated in an article of clothing worn near the head, such as a hat, headband, etc.

In an example where the eye-mountable device 810 includes an analyte bio-sensor 862, the system 800 can be operated to monitor the analyte concentration in tear film on the surface of the eye. Thus, the eye-mountable device 810 can be configured as a platform for an ophthalmic analyte bio-sensor. The tear film is an aqueous layer secreted from the lacrimal gland to coat the eye. The tear film is in contact with the blood supply through capillaries in the structure of the eye and includes many biomarkers found in blood that are analyzed to characterize a person's health condition(s). For example, the tear film includes glucose, calcium, sodium, cholesterol, potassium, other biomarkers, etc. The biomarker concentrations in the tear film can be systematically different than the corresponding concentrations of the biomarkers in the blood, but a relationship between the two concentration levels can be established to map tear film biomarker concentration values to blood concentration levels. For example, the tear film concentration of glucose can be established (e.g., empirically determined) to be approximately one tenth the corresponding blood glucose concentration. Thus, measuring tear film analyte concentration levels provides a non-invasive technique for monitoring biomarker levels in comparison to blood sampling techniques performed by lancing a volume of blood to be analyzed outside a person's body. Moreover, the ophthalmic analyte bio-sensor platform disclosed here can be operated substantially continuously to enable real time monitoring of analyte concentrations.

To perform a reading with the system 800 configured as a tear film analyte monitor, the external reader 880 can emit radio frequency radiation 871 that is harvested to power the eye-mountable device 810 via the power supply 840. Radio frequency electrical signals captured by the energy harvesting antenna 842 (and/or the antenna 870) are rectified and/or regulated in the rectifier/regulator 846 and a regulated DC supply voltage 847 is provided to the controller 850. The radio frequency radiation 871 thus turns on the electronic components within the eye-mountable device 810. Once turned on, the controller 850 operates the analyte bio-sensor 862 to measure an analyte concentration level. For example, the sensor interface module 852 can apply a voltage between a working electrode and a reference electrode in the analyte bio-sensor 862 sufficient to cause the analyte to undergo an electrochemical reaction at the working electrode. The current through the working electrode can be measured to provide the sensor output indicative of the analyte concentration. The controller 850 can operate the antenna 870 to communicate the sensor results back to the external reader 880 (e.g., via the communication circuit 856). The sensor result can be communicated by, for example, modulating an impedance of the antenna 870 such that the modulation in impedance is detected by the external reader 880. The modulation in antenna impedance can be detected by, for example, backscatter radiation from the antenna 870.

In some embodiments, the system 800 can operate to non-continuously ("intermittently") supply energy to the eye-mountable device 810 to power the on-board controller 850 and electronics 860. For example, radio frequency radiation 871 can be supplied to power the eye-mountable device 810 long enough to carry out a tear film analyte concentration measurement and communicate the results. For example, the supplied radio frequency radiation can provide sufficient power to charge two electrodes to a potential sufficient to induce electrochemical reactions, measure the resulting amperometric current, and modulate the antenna impedance to adjust the backscatter radiation in a manner indicative of the measured current. In such an example, the supplied radio frequency radiation 871 can be considered an interrogation signal from the external reader 880 to the eye-mountable device 810 to request a measurement. By periodically interrogating the eye-mountable device 810 (e.g., by supplying radio frequency radiation 871 to temporarily turn the device on) and storing the sensor results (e.g., via the data storage 883), the external reader 880 can accumulate a set of analyte concentration measurements over time without continuously powering the eye-mountable device 810.

Figure 9A:
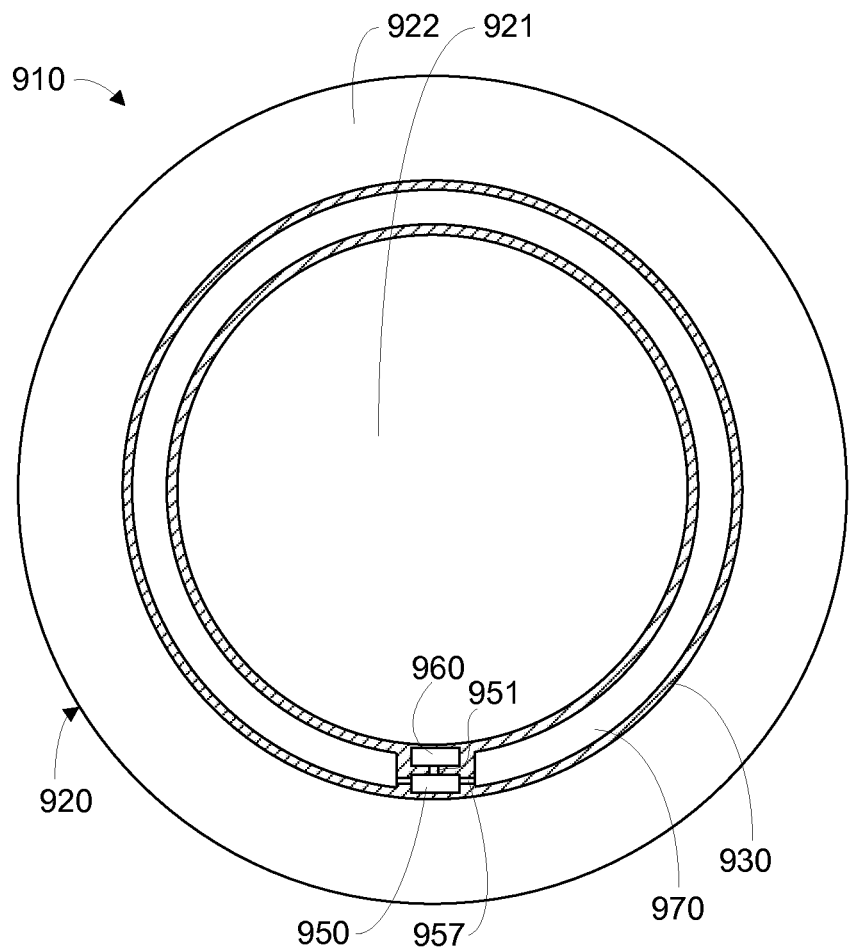
FIG. 9a is a top view of an eye-mountable device, according to an example embodiment.
Figure 9B:
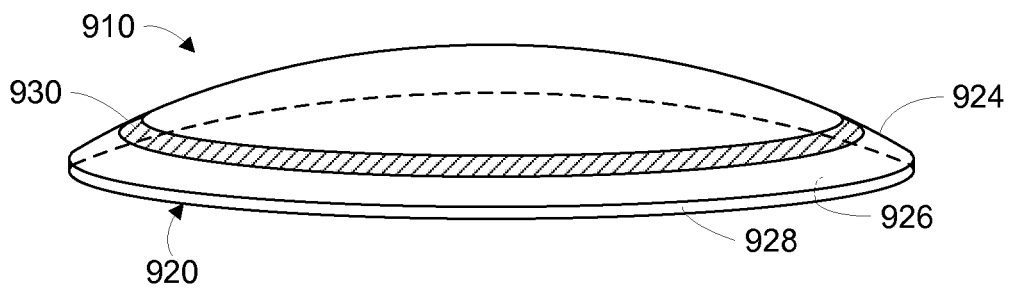
FIG. 9b is a side view of an eye-mountable device, according to an example embodiment.

FIG. 9a is a top view of an eye-mountable electronic device 910. FIG. 9b is a side view of the eye-mountable electronic device shown in FIG. 9a. It is noted that relative dimensions in FIGS. 9a and 9b are not necessarily to scale, but have been rendered for purposes of explanation only in describing the arrangement of the eye-mountable electronic device 910. The eye-mountable device 910 is formed of a polymeric material 920 shaped as a curved disk. The polymeric material 920 can be a substantially transparent material to allow incident light to be transmitted to the eye while the eye-mountable device 910 is mounted to the eye. The polymeric material 920 can be a biocompatible material similar to those employed to form vision correction and/or cosmetic contact lenses in optometry, such as PET, polymethyl methacrylate ("PMMA"), silicone hydrogels, combinations of these, etc. The polymeric material 920 can be formed with one side having a concave surface 926 suitable to fit over a corneal surface of an eye. The opposing side of the disk can have a convex surface 924 that does not interfere with eyelid motion while the eye-mountable device 910 is mounted to the eye. A circular outer side edge 928 connects the concave surface 924 and convex surface 926.

The eye-mountable device 910 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of the eye-mountable device 910 can be selected according to the size and/or shape of the corneal surface and/or the scleral surface of the wearer's eye.

While the eye-mountable device 910 is mounted in an eye, the convex surface 924 (i.e., the anterior surface) faces outward to the ambient environment while the concave surface 926 (i.e., the posterior surface) faces inward, toward the corneal surface. The convex surface 924 can therefore be considered an outer, top surface of the eye-mountable device 910 whereas the concave surface 926 can be considered an inner, bottom surface. The "top" view shown in FIG. 9a is facing the convex surface 924.

A substrate 930 is embedded in the polymeric material 920. The substrate 930 can be embedded to be situated along the outer periphery 922 of the polymeric material 920, away from the center region 921. The substrate 930 does not interfere with vision because it is too close to the eye to be in focus and is positioned away from the center region 921 where incident light is transmitted to the light-sensing portions of the eye. Moreover, the substrate 930 can be formed of a transparent material to further mitigate any effects on visual perception.

The substrate 930 can be shaped as a flat, circular ring (e.g., a disk with a central hole). The flat surface of the substrate 930 (e.g., along the radial width) is a platform for mounting electronics such as chips (e.g., via flip-chip mounting) and for patterning conductive materials (e.g., via deposition techniques) to form electrodes, antenna(e), and/or connections. The substrate 930 and the polymeric material 920 can be approximately cylindrically symmetric about a common central axis. The substrate 930 can have, for example, a diameter of about 10 millimeters, a radial width of about 1 millimeter (e.g., an outer radius 1 millimeter greater than an inner radius), and a thickness of about 50 micrometers. However, these dimensions are provided for example purposes only. The substrate 930 can be implemented in a variety of different form factors.

A loop antenna 970, a controller 950, and bio-interactive electronics 960 are disposed on the embedded substrate 930. The controller 950 can be a chip including logic elements configured to operate the bio-interactive electronics 960 and the loop antenna 970. The controller 950 is electrically connected to the loop antenna 970 by interconnects 957 also situated on the substrate 930. Similarly, the controller 950 is electrically connected to the bio-interactive electronics 960 by interconnects 951. The interconnects 951, 957, the loop antenna 970, and any conductive electrodes (e.g., for an electrochemical analyte bio-sensor, etc.) can be formed from conductive materials patterned on the substrate 930 by a process for precisely patterning such materials, such as deposition or lithography. The conductive materials patterned on the substrate 930 can be, for example, gold, platinum, palladium, titanium, carbon, aluminum, copper, silver, silver-chloride, and/or other materials.

With reference to FIG. 9a, which is a view facing the convex surface 924 of the eye-mountable device 910, the bio-interactive electronics 960 is mounted to a side of the substrate 930 facing the convex surface 924. Where the bio-interactive electronics 960 includes an analyte bio-sensor, for example, mounting such a bio-sensor on the substrate 930 facing the convex surface 924 allows the bio-sensor to receive analyte concentrations in tear film through a channel 972 in the polymeric material 920 to the convex surface 924 (as shown in FIGS. 9c and 9d). In some embodiments, some electronic components can be mounted on one side of the substrate 930, while other electronic components are mounted to the opposing side, and connections between the two can be made through conductive materials passing through the substrate 930.

The loop antenna 970 is a layer of conductive material patterned along the flat surface of the substrate to form a flat conductive ring. In some instances, the loop antenna 970 can be formed without making a complete loop. For instance, the loop antenna 970 can have a cutout to allow room for the controller 950 and the bio-interactive electronics 960, as illustrated in FIG. 9a. However, the loop antenna 970 can also be arranged as a continuous strip of conductive material that wraps entirely around the flat surface of the substrate 930 one or more times. For example, a strip of conductive material with multiple windings can be patterned on the side of the substrate 930 opposite the controller 950 and bio-interactive electronics 960. Interconnects between the ends of such a wound antenna (e.g., the antenna leads) can be passed through the substrate 930 to the controller 950. In some embodiments, the loop antenna can include a plurality of conductive loops spaced apart from each other, such as three conductive loops, five conductive loops, nine conductive loops, etc. With such an arrangement, the polymeric material 920 may extend between adjacent conductive loops in the plurality of conductive loops.

FIG. 9c is a side cross-section view of the eye-mountable electronic device 910 while mounted to a corneal surface 984 of an eye 980. FIG. 9d is a close-in side cross-section view enhanced to show tear film layers 990, 992 surrounding the exposed surfaces 924, 926 of the eye-mountable device 910. It is noted that relative dimensions in FIGS. 9c and 9d are not necessarily to scale, but have been rendered for purposes of explanation only in describing the arrangement of the eye-mountable electronic device 910. For example, the total thickness of the eye-mountable device 910 can be about 200 micrometers, while the thickness of the tear film layers 990, 992 can each be about 10 micrometers, although this ratio may not be reflected in the drawings. Some aspects are exaggerated to allow for illustration and facilitate explanation.

The eye 980 includes a cornea 982 that is covered by bringing the upper eyelid 986 and lower eyelid 988 together over the top of the eye 980. Incident light is received by the eye 980 through the cornea 982, where light is optically directed to light sensing elements of the eye 980 (e.g., rods and cones, etc.) to stimulate visual perception. The motion of the eyelids 986, 988 distributes a tear film across the exposed corneal surface 984 of the eye 980. The tear film is an aqueous solution secreted by the lacrimal gland to protect and lubricate the eye 980. When the eye-mountable device 910 is mounted in the eye 980, the tear film coats both the convex and concave surfaces 924, 926 with an inner layer 990 (along the concave surface 926) and an outer layer 992 (along the convex layer 924). The tear film layers 990, 992 can be about 10 micrometers in thickness and together account for about 10 microliters.

The tear film layers 990, 992 are distributed across the corneal surface 984 and/or the convex surface 924 by motion of the eyelids 986, 988. For example, the eyelids 986, 988 raise and lower, respectively, to spread a small volume of tear film across the corneal surface 984 and/or the convex surface 924 of the eye-mountable device 910. The tear film layer 990 on the corneal surface 984 also facilitates mounting the eye-mountable device 910 by capillary forces between the concave surface 926 and the corneal surface 984. In some embodiments, the eye-mountable device 910 can also be held over the eye in part by vacuum forces against the corneal surface 984 due to the concave curvature of the eye-facing concave surface 926.

As shown in the cross-sectional views in FIGS. 9c and 9d, the substrate 930 can be inclined such that the flat mounting surfaces of the substrate 930 are approximately parallel to the adjacent portion of the convex surface 924. As described above, the substrate 930 is a flattened ring with an inward-facing surface 932 (facing the concave surface 926 of the polymeric material 920) and an outward-facing surface 934 (facing the convex surface 924). The substrate 930 can have electronic components and/or patterned conductive materials mounted to either or both mounting surfaces 932, 934.

As shown in FIG. 9d, the bio-interactive electronics 960, the controller 950, and the conductive interconnect 951 are located between the outward-facing surface 934 and the inward-facing surface 932 such that the bio-interactive electronics 960 are facing the convex surface 924. As described above, the polymer layer defining the anterior side may be greater than 50 micrometers thick, whereas the polymer layer defining the posterior side may be less than 150 micrometers. Thus, the bio-interactive electronics 960 may be at least 50 micrometers away from the convex surface 924 and may be a greater distance away from the concave surface 926. However, in other examples, the bio-interactive electronics 960 may be mounted on the inward-facing surface 932 of the substrate 930 such that the bio-interactive electronics 960 are facing the concave surface 926. The bio-interactive electronics 960 could also be positioned closer to the concave surface 926 than the convex surface 924. With this arrangement, the bio-interactive electronics 960 can receive analyte concentrations in the tear film 992 through the channel 972.

While the body-mountable device has been described as comprising the eye-mountable device 810 and/or the eye-mountable device 910, the body-mountable device could comprise other mountable devices that are mounted on or in other portions of the body.

As noted, in some embodiments, the body-mountable device may comprise a tooth-mountable device. In some embodiments, the tooth-mountable device may take the form of or be similar in form to the eye-mountable device 810 and/or the eye-mountable device 910. For instance, the tooth-mountable device may include a polymeric material that is the same or similar to any of the polymeric materials described herein and a substrate that is the same or similar to any of the substrates described herein.

As noted, in some embodiments, the body-mountable device may comprise a skin-mountable device. In some embodiments, the skin-mountable device may take the form of or be similar in form to the eye-mountable device 810 and/or the eye-mountable device 910. For instance, the skin-mountable device may include a polymeric material that is the same or similar to any of the polymeric materials described herein and a substrate that is the same or similar to any of the substrates described herein.

IV. Conclusion

It should be understood that arrangements described herein are for purposes of example only. As such, those skilled in the art will appreciate that other arrangements and other elements (e.g., machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

Where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The invention claimed is:

1. A method comprising:
   forming a first polymer layer;
   positioning a structure on the first polymer layer, wherein the structure comprises a sensor;
   forming, in a molding piece, a body-mountable device by forming a second polymer layer over the structure positioned on the first polymer layer, wherein the first polymer layer defines a first side of the body-mountable device and the second polymer layer defines a second side of the body-mountable device opposite the first side, and wherein the molding piece comprises a surface that supports the second polymer layer as the second polymer layer is being formed and a protrusion that extends from the surface to the sensor through the second polymer layer as the second polymer layer is being formed; and
   removing the body-mountable device from the molding piece, wherein the body-mountable device removed from the molding piece has a channel to the sensor formed by the protrusion.

2. The method of claim 1, wherein the protrusion comprises a rod and a spring, wherein the rod has a first end and a second end, and wherein the spring is connected to the second end of the rod and configured to press the first end of the rod against the sensor during formation of the second polymer layer.

3. The method of claim 2, wherein the first end of the rod comprises a compliant material.

4. The method of claim 3, wherein the compliant material fully covers the sensor during formation of the second polymer layer.

5. The method of claim 2, wherein the rod comprises a complaint material.

6. The method of claim 2, wherein the first end of the rod is wider than the sensor.

7. The method of claim 6, wherein the second end of the rod is wider than the first end of the rod.

8. The method of claim 2, wherein a dimension of the rod defines a dimension of the channel.

9. The method of claim 8, wherein a dimension of the first end of the rod defines a dimension of the channel.

10. The method of claim 2, wherein the spring is further configured to deform a distance when pressing the first end of the rod against the sensor during formation of the second polymer layer.

11. The method of claim 2, further comprising:
    applying a non-stick coating to at least one of the sensor or the rod.

12. The method of claim 1, wherein forming the second polymer layer over the structure positioned on the first polymer layer comprises:
    providing a polymer material on the surface of the molding piece;
    orienting an additional molding piece over the polymer material on the surface of the molding piece, wherein the additional molding piece holds the structure positioned on the first polymer layer, and wherein the orienting of the additional molding piece positions the sensor directly above the protrusion;
    bringing the molding piece and the oriented additional molding piece together into a forming position, wherein in the forming position (i) the polymer material on the surface of the molding piece contacts the structure and the first polymer layer held by the additional molding piece and (ii) the sensor contacts the protrusion; and
    in the forming position, curing the polymer material to form the second polymer layer.

13. The method of claim 12, wherein the protrusion comprises a rod having a first end, and wherein providing the polymer material on the surface of the molding piece comprises providing the polymer material on the surface of the molding piece, such that the first end of the rod is located above the polymer material.

14. The method of claim 13, wherein the rod is moveable, and wherein bringing the molding piece and the oriented second molding piece together into the forming position moves the rod downward such that a portion of the first end of the rod is substantially flush with a surface of the polymer material.

\* \* \* \* \*